United States Patent
Fukunishi et al.

(10) Patent No.: US 10,379,058 B2
(45) Date of Patent: Aug. 13, 2019

(54) MEASUREMENT DEVICE AND METHOD FOR OPERATING THE SAME

(71) Applicant: OLYMPUS CORPORATION, Tokyo (JP)

(72) Inventors: Munenori Fukunishi, Tokyo (JP);
Naoyuki Miyashita, Tokorozawa (JP);
Kiyotomi Ogawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/996,595

(22) Filed: Jun. 4, 2018

(65) Prior Publication Data

US 2018/0364178 A1 Dec. 20, 2018

(30) Foreign Application Priority Data

Jun. 14, 2017 (JP) .................. 2017-116591

(51) Int. Cl.
*G01N 21/954* (2006.01)
*G01N 21/88* (2006.01)

(52) U.S. Cl.
CPC ....... *G01N 21/8806* (2013.01); *G01N 21/954* (2013.01); *G01N 2021/9542* (2013.01)

(58) Field of Classification Search
CPC ............. G01N 21/8806; G01N 21/954; G01N 2021/9542

USPC ....................................................... 356/241.1
See application file for complete search history.

(56) References Cited

U.S. PATENT DOCUMENTS

| 2010/0208046 A1* | 8/2010 | Takahashi | A61B 1/00193 348/65 |
|---|---|---|---|
| 2014/0049657 A1 | 2/2014 | Fukunishi | |
| 2018/0128736 A1* | 5/2018 | Kanamori | A61B 3/117 |
| 2018/0197306 A1* | 7/2018 | Fukunishi | H04N 5/23267 |

FOREIGN PATENT DOCUMENTS

| JP | 2004-049638 A | 2/2004 |
|---|---|---|
| JP | 2010-128354 A | 6/2010 |
| JP | 5744614 B2 | 7/2015 |
| JP | 2016-014896 A | 1/2016 |

* cited by examiner

*Primary Examiner* — Roy M Punnoose
(74) *Attorney, Agent, or Firm* — Scully, Scott, Murphy & Presser, P.C.

(57) ABSTRACT

In a measurement device, an imaging unit generates a first image and a second image. A subject distance detection unit detects a subject distance. A motion detection unit detects an amount of motion of the imaging unit. A measurement availability determination unit determines whether or not measurement is executable by comparing the amount of motion with an allowable threshold value according to the subject distance. A measurement processing unit executes a measurement process on the basis of the first image and the second image when the measurement availability determination unit determines that the measurement is executable.

12 Claims, 16 Drawing Sheets

● DETECTION SUCCESS (HIGH RELIABILITY)
○ DETECTION FAILURE (LOW RELIABILITY)

FIG. 10

| SUBJECT DISTANCE | ALLOWABLE THRESHOLD VALUE |
|---|---|
| ~10mm | <1.0 PIXEL |
| ~20mm | <0.5 PIXELS |
| ~30mm | <0.3 PIXELS |
| ~40mm | <0.2 PIXELS |
| ~50mm | <0.2 PIXELS |
| 50~mm | <0.2 PIXELS |

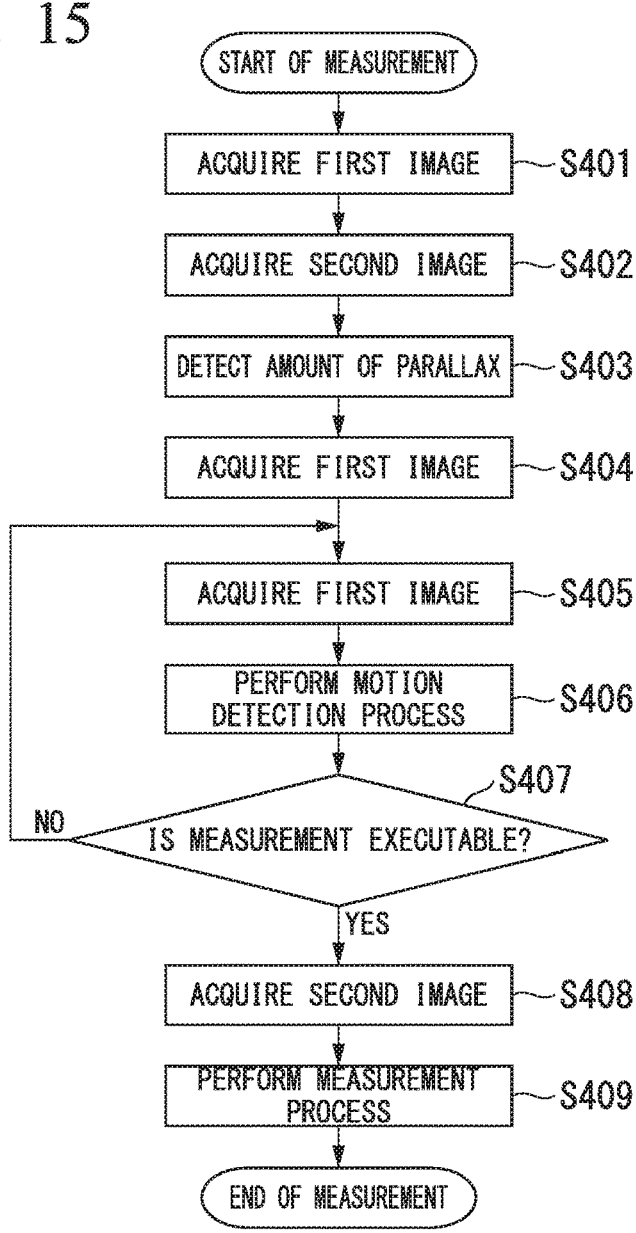

MEASUREMENT DEVICE AND METHOD FOR OPERATING THE SAME

BACKGROUND OF THE INVENTION

Field of the Invention

The present invention relates to a measurement device and a method for operating the same.

Priority is claimed on Japanese Patent Application No. 2017-116591, filed on Jun. 14, 2017, the content of which is incorporated herein by reference.

Description of Related Art

Industrial endoscopes are widely used for nondestructively performing visual inspection for internal scratches and corrosion of engines, turbines, chemical plants, and the like. When defects such as scratches and corrosion are found, it is necessary to perform switching between countermeasure methods according to a degree thereof. Thus, there is an industrial endoscope having a measurement function of measuring the scale of scratches and corrosion.

For example, as shown in Japanese Unexamined Patent Application, First Publication No. 2004-49638, a measurement endoscope device includes two optical systems having parallax. The measurement endoscope device simultaneously captures optical images obtained by the optical systems. The measurement endoscope device calculates three-dimensional coordinates of a subject and a size of the subject on the basis of the principle of stereo measurement using the two generated images.

A stereo measurement device disclosed in Japanese Unexamined Patent Application, First Publication No. 2010-128354 includes an optical system configured to form two images of a subject formed by light passing through two different optical paths (referred to as a first optical path and a second optical path) in a common region of an imaging element. Also, the stereo measurement device includes an optical path switching means for performing switching between the optical paths so that a subject image formed only by light passing through one of the two optical paths is captured.

When a subject is measured using the stereo measurement device disclosed in Japanese Unexamined Patent Application, First Publication No. 2010-128354, an image (referred to as a first image) is generated through imaging based on a first subject image formed by light passing through the first optical path. Subsequently, the optical path is switched and an image (referred to as a second image) is generated through imaging based on a second subject image formed by light passing through the second optical path. On the basis of parallaxes of the first image and the second image, a shape of the subject is measured using the principle of stereo measurement.

In a measurement endoscope device disclosed in Japanese Unexamined Patent Application, First Publication No. 2004-49638, two subject images formed by light passing through two optical paths are formed in different regions of an imaging element. On the other hand, in a stereo measurement device disclosed in Japanese Unexamined Patent Application, First Publication No. 2010-128354, two subject images formed by light passing through two optical paths are formed in a common region of an imaging element. Thus, in the stereo measurement device disclosed in Japanese Unexamined Patent Application, First Publication No. 2010-128354, it is possible to increase an imaging area and improve imaging quality.

On the other hand, according to a technique of Japanese Unexamined Patent Application, First Publication No. 2010-128354, an error may occur in parameters (a baseline length and the like) of stereo measurement due to movement of an endoscope while a first image and a second image are captured. Thus, it is not possible to accurately measure a shape of a subject. A technique for solving this problem is disclosed in Japanese Unexamined Patent Application, First Publication No. 2016-14896.

An endoscope device disclosed in Japanese Unexamined Patent Application, First Publication No. 2016-14896 alternately captures a first image and a second image. When an amount of displacement between two first images or between two second images is less than a predetermined threshold value, the endoscope device determines that there is no motion in the device and performs a measurement process.

SUMMARY OF THE INVENTION

According to a first aspect of the present invention, a measurement device includes an imaging unit, a subject distance detection unit, a motion detection unit, a measurement availability determination unit, and a measurement processing unit. The imaging unit captures a first subject image via a first objective optical system at a first imaging timing. The imaging unit captures a second subject image via a second objective optical system at a second imaging timing different from the first imaging timing. The imaging unit generates a first image based on the first subject image. The imaging unit generates a second image based on the second subject image. The second objective optical system is arranged to have parallax with respect to the first objective optical system. The subject distance detection unit detects a subject distance. The motion detection unit detects an amount of motion of the imaging unit. The measurement availability determination unit determines whether or not measurement is executable by comparing the amount of motion with an allowable threshold value according to the subject distance. The measurement processing unit executes a measurement process on the basis of the first image and the second image when the measurement availability determination unit determines that the measurement is executable.

According to a second aspect of the present invention, in the first aspect, the subject distance detection unit may detect the subject distance by at least one of stereo measurement using the first image and the second image and laser length measurement.

According to a third aspect of the present invention, in the first aspect, the motion detection unit may detect the amount of motion by detecting an amount of displacement between a plurality of the first images.

According to a fourth aspect of the present invention, in the first aspect, the motion detection unit may be at least one of an acceleration sensor and a gyro sensor.

According to a fifth aspect of the present invention, in the first aspect, the measurement device may further include a storage unit configured to store a table in which the subject distance and the allowable threshold value are associated. The measurement availability determination unit may acquire the allowable threshold value corresponding to the subject distance detected by the subject distance detection unit from the table.

According to a sixth aspect of the present invention, in the first aspect, the measurement availability determination unit may calculate the allowable threshold value corresponding to the subject distance on the basis of an amount of errors in a result of the measurement process. The amount of errors may be predetermined for each subject distance.

According to a seventh aspect of the present invention, in the first aspect, a first allowable threshold value as the allowable threshold value corresponding to a first subject distance may be greater than a second allowable threshold value as the allowable threshold value corresponding to a second subject distance greater than the first subject distance.

According to an eighth aspect of the present invention, a measurement device includes an imaging unit, a parallax detection unit, a motion detection unit, a measurement availability determination unit, and a measurement processing unit. The imaging unit captures a first subject image via a first objective optical system at a first imaging timing. The imaging unit captures a second subject image via a second objective optical system at a second imaging timing different from the first imaging timing. The imaging unit generates a first image based on the first subject image. The imaging unit generates a second image based on the second subject image. The second objective optical system is arranged to have parallax with respect to the first objective optical system. The parallax detection unit detects an amount of parallax between the first image and the second image. The motion detection unit detects an amount of motion of the imaging unit. The measurement availability determination unit determines whether or not measurement is executable by comparing the amount of motion with an allowable threshold value according to the amount of parallax. The measurement processing unit executes a measurement process on the basis of the first image and the second image when the measurement availability determination unit determines that the measurement is executable.

According to a ninth aspect of the present invention, in the eighth aspect, the measurement device may further include a storage unit configured to store a table in which the amount of parallax and the allowable threshold value are associated. The measurement availability determination unit may acquire the allowable threshold value corresponding to the amount of parallax detected by the parallax detection unit from the table.

According to a tenth aspect of the present invention, in the eighth aspect, the measurement availability determination unit may calculate the allowable threshold value corresponding to the amount of parallax on the basis of an amount of errors in a result of the measurement process. The amount of errors may be predetermined for each amount of parallax.

According to an eleventh aspect of the present invention, in the eighth aspect, a first allowable threshold value as the allowable threshold value corresponding to a first amount of parallax may be greater than a second allowable threshold value as the allowable threshold value corresponding to a second amount of parallax less than the first amount of parallax.

According to a twelfth aspect of the present invention, a measurement device includes an imaging unit, a motion detection unit, a measurement processing unit, and a validity determination unit. The imaging unit captures a first subject image via a first objective optical system at a first imaging timing. The imaging unit captures a second subject image via a second objective optical system at a second imaging timing different from the first imaging timing. The imaging unit generates a first image based on the first subject image. The imaging unit generates a second image based on the second subject image. The second objective optical system is arranged to have parallax with respect to the first objective optical system. The motion detection unit detects an amount of motion of the imaging unit. The measurement processing unit executes a measurement process on the basis of the first image and the second image and detects a subject distance in the measurement process. The validity determination unit determines validity of a result of the measurement process by comparing the amount of motion with an allowable threshold value according to the subject distance.

BRIEF DESCRIPTION OF THE DRAWINGS

FIG. 10 is a diagram showing a table in the first embodiment of the present invention.

FIG. 15 is a flowchart showing a measurement procedure in the second embodiment of the present invention.

FIG. 16 is a diagram showing a table in the second embodiment of the present invention.

DETAILED DESCRIPTION OF THE INVENTION

Hereinafter, embodiments of the present invention will be described with reference to the drawings.

First Embodiment

Figure 1:
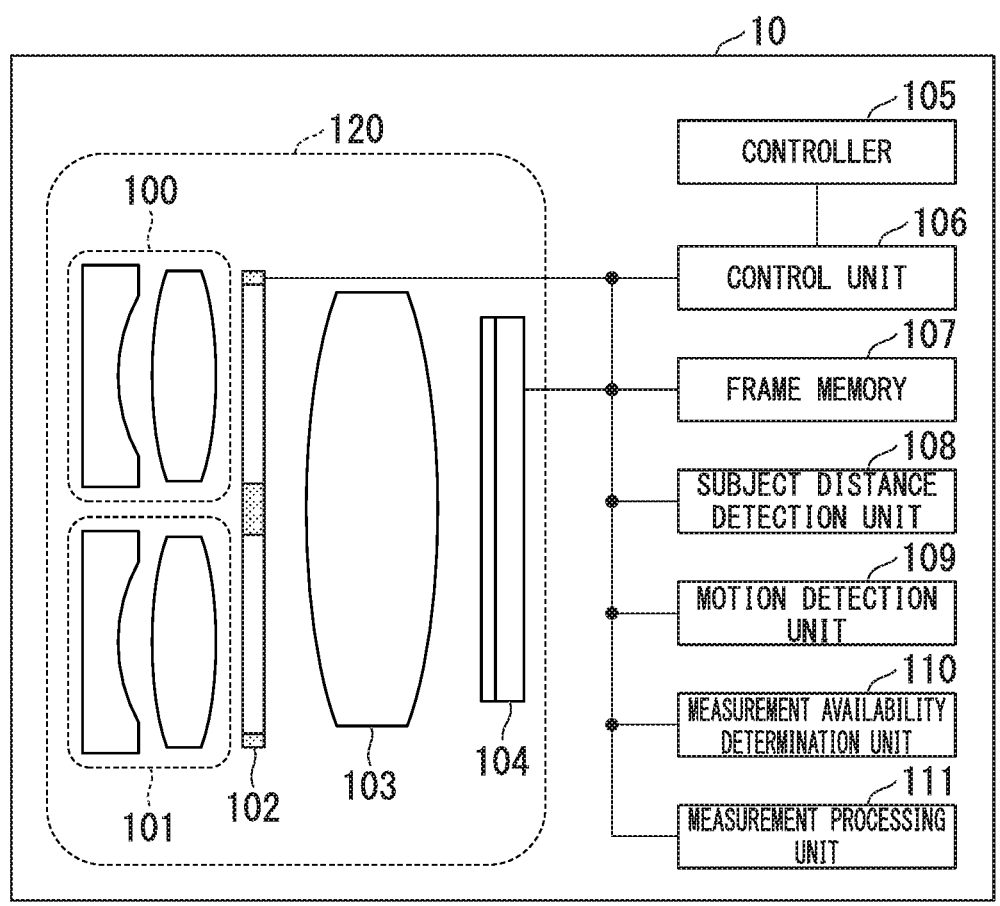
FIG. 1 is a block diagram showing a configuration of a measurement device according to a first embodiment of the present invention.

FIG. 1 shows a configuration of a measurement device 10 according to a first embodiment of the present invention. For example, the measurement device 10 is an endoscope device including an insertion portion to be inserted into an object to be measured. As shown in FIG. 1, the measurement device 10 includes a first objective optical system 100, a second objective optical system 101, an optical path switching unit 102, an image forming optical system 103, an imaging element 104 (an imaging unit), a controller 105, a control unit 106, a frame memory 107 (a storage unit), a subject distance detection unit 108, a motion detection unit 109, a measurement availability determination unit 110, and a measurement processing unit 111.

For example, the first objective optical system 100 and the second objective optical system 101 include an objective lens in which a concave lens and a convex lens are combined. The second objective optical system 101 is arranged to have parallax with respect to the first objective optical system 100. That is, the first objective optical system 100 and the second objective optical system 101 are separated in a parallax direction. The parallax direction is a direction of a straight line passing through an optical center (a principal point) of the first objective optical system 100 and an optical center (a principal point) of the second objective optical system 101. Light incident on the first objective optical system 100 passes through a first optical path. Light incident on the second objective optical system 101 passes through a second optical path different from the first optical path. The first objective optical system 100 forms a first subject image and the second objective optical system 101 forms a second subject image.

The optical path switching unit 102 performs switching between the first optical path and the second optical path so that only one of the first subject image and the second subject image is formed on the imaging element 104. When the optical path switching unit 102 transmits the light of the first optical path, the light of the second optical path is shielded. When the optical path switching unit 102 transmits the light of the second optical path, the light of the first optical path is shielded. An optical path switching operation of the optical path switching unit 102 is controlled by a control signal from the control unit 106. The image forming optical system 103 forms a subject image based on either light passing through the first optical path or light passing through the second optical path on the surface of the imaging element 104.

The imaging element 104 captures a first subject image via the first objective optical system 100 at a first imaging timing. The imaging element 104 captures a second subject image via the second objective optical system 101 at a second imaging timing different from the first imaging timing. The imaging element 104 generates a first image based on the first subject image. The imaging element 104 generates a second image based on the second subject image. The imaging element 104 captures the first subject image at a plurality of first imaging timings different from one another and generates a plurality of first images. The first objective optical system 100, the second objective optical system 101, the optical path switching unit 102, the image forming optical system 103, and the imaging element 104 constitute a scope 120. For example, in the endoscope device, the scope 120 is arranged in the insertion portion.

The controller 105 is an operation unit (a user interface) to be operated by a user. For example, the operation unit is at least one of buttons, switches, keys, a mouse, a joystick, a touch pad, a track ball, and a touch panel. The controller 105 receives an instruction such as "start photographing," "start measurement," "stop photographing", or "acquire measurement result" from the user. The controller 105 outputs a command corresponding to the instruction received from the user to the control unit 106.

The command from the controller 105 is input to the control unit 106. The control unit 106 transmits a control signal corresponding to the command to each part according to a state of each part to be described below and controls a series of processing sequences for measuring a subject shape and a subject distance. The subject distance is a distance from the scope 120 in which the imaging element 104 is arranged or the imaging element 104 to the subject. The frame memory 107 stores the first image and the second image generated by the imaging element 104. Also, the frame memory 107 stores a table in which subject distances and allowable threshold values are associated.

The frame memory 107 is configured as a volatile or nonvolatile memory. For example, the frame memory 107 may be at least one of a random access memory (RAM), a dynamic random access memory (DRAM), a static random access memory (SRAM), an erasable programmable read only memory (EPROM), an electrically erasable programmable read only memory (EEPROM), and a flash memory. The measurement device 10 may have a hard disk drive for storing the table in which subject distances and allowable threshold values are associated.

The subject distance detection unit 108 detects the subject distance. In the example shown in FIG. 1, the subject distance detection unit 108 detects the subject distance by stereo measurement using the first image and the second image. Therefore, the subject distance detection unit 108 detects a distance from the imaging element 104 to the subject as the subject distance. The measurement processing unit 111 may have a function of the subject distance detection unit 108.

The subject distance detection unit 108 may detect the subject distance by using a laser length measurement means or the like. In this case, the subject distance detection unit 108 may be arranged in the scope 120 together with the imaging element 104 and may detect the distance from the subject distance detection unit 108 to the subject as the subject distance. The subject distance detection unit 108 may detect the subject distance by at least one of stereo measurement and laser length measurement.

The motion detection unit 109 detects an amount of motion of the imaging element 104. In the example shown in FIG. 1, the motion detection unit 109 detects the amount of motion by detecting an amount of displacement between a plurality of first images. The motion detection unit 109 may be at least one of an acceleration sensor and a gyro sensor arranged in the scope 120 together with the imaging element 104. In this case, the imaging element 104 and the motion detection unit 109 are fixed to the scope 120. The motion detection unit 109 outputs a signal based on the amount of motion of the imaging element 104.

The measurement availability determination unit 110 determines whether or not measurement is executable by comparing the amount of motion detected by the motion detection unit 109 with an allowable threshold value according to the subject distance detected by the subject distance detection unit 108. The measurement availability determination unit 110 obtains an allowable threshold value corresponding to the subject distance detected by the subject distance detection unit 108 from the table stored in the frame memory 107.

The measurement processing unit 111 executes a measurement process on the basis of the first image and the second image when the measurement availability determination unit 110 determines that the measurement is executable. The measurement processing unit 111 calculates at least one of the subject shape and the subject distance through the measurement process. For example, the subject distance is a distance between any two points.

In the example shown in FIG. 1, the control unit 106, the subject distance detection unit 108, the motion detection unit 109, the measurement availability determination unit 110, and the measurement processing unit 111 may include at least one of a processor and a logic circuit. For example, the processor is at least one of a central processing unit (CPU), a digital signal processor (DSP), and a graphics processing unit (GPU). For example, the logic circuit is at least one of an application specific integrated circuit (ASIC) and a field-programmable gate array (FPGA). The control unit 106, the subject distance detection unit 108, the motion detection unit 109, the measurement availability determination unit 110, and the measurement processing unit 111 can include one or more processors. The control unit 106, the subject distance detection unit 108, the motion detection unit 109, the measurement availability determination unit 110, and the measurement processing unit 111 can include one or more logic circuits.

A computer of the measurement device 10 may read a program including commands defining the operations of the control unit 106, the subject distance detection unit 108, the motion detection unit 109, the measurement availability determination unit 110, and the measurement processing unit 111, and execute the read program. That is, the functions of the control unit 106, the subject distance detection unit 108, the motion detection unit 109, the measurement availability determination unit 110, and the measurement processing unit 111 may be implemented by software. For example, this program may be provided by a "computer-readable recording medium" such as a flash memory. The above-described program may be transmitted from a computer having a storage device or the like in which the program is stored to the measurement device 10 via a transmission medium or transmission waves in the transmission medium. The "transmission medium" for transmitting the program refers to a medium having an information transmission function, for example, a network (a communication network) such as the Internet or a communication circuit (a communication line) such as a telephone circuit. Also, the above-described program may be a program for implementing some of the above-described functions. Further, the above-described program may be a program capable of implementing the above-described function in combination with a program already recorded on the computer, i.e., a so-called differential file (differential program).

The allowable threshold value included in the table stored in the frame memory 107 differs according to the subject distance. For example, the allowable threshold value corresponding to a subject distance in which the amount of motion is large but measurement accuracy would be difficult to decrease may be set to a large value. Also, the allowable threshold value corresponding to a subject distance in which the amount of motion is small but measurement accuracy would be easy to decrease may be set to a small value. Thereby, it is possible to secure a desired measurement accuracy and increase a frequency of execution of measurement.

Figure 2A:
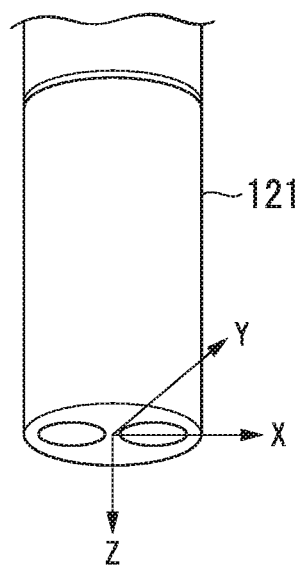
FIG. 2A is an exterior diagram of an optical adapter in the first embodiment of the present invention.
Figure 2B:
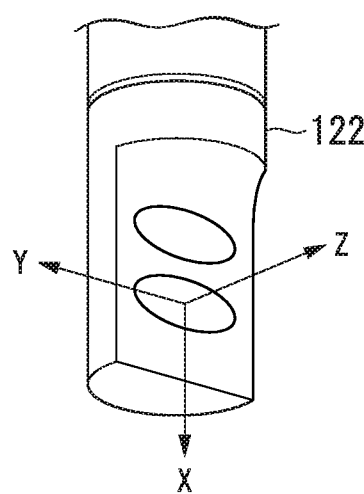
FIG. 2B is an exterior diagram of an optical adapter in the first embodiment of the present invention.

In an industrial endoscope, an optical adapter of a tip of the scope 120 can be exchanged to implement an appropriate observation direction according to the subject. The optical adapter includes the first objective optical system 100 and the second objective optical system 101. For example, the exchange type optical adapter includes a direct-view adapter and a side-view adapter. FIGS. 2A and 2B are exterior diagrams of the optical adapter. An optical adapter 121 shown in FIG. 2A is a direct-view adapter. An optical adapter 122 shown in FIG. 2B is a side-view adapter.

A direct-view adapter is an optical adapter for observing in a tip direction of the scope 120. A side-view adapter is an optical adapter for observing in a side direction of the scope 120. In FIGS. 2A and 2B, the observation directions of the optical adapter 121 and the optical adapter 122 are a Z-axis direction.

A motion of the imaging element 104 can be resolved into six motions of movements in axial directions of a Z axis, a Y axis, and an X axis, and rotations around these axes. Here, the motion of the imaging element 104 to be detected is translational movement in X-axis and Y-axis directions orthogonal to the optical axis. In the direct-view adapter, in particular, translational deviations in the X and Y axis directions are dominant.

Figure 3:
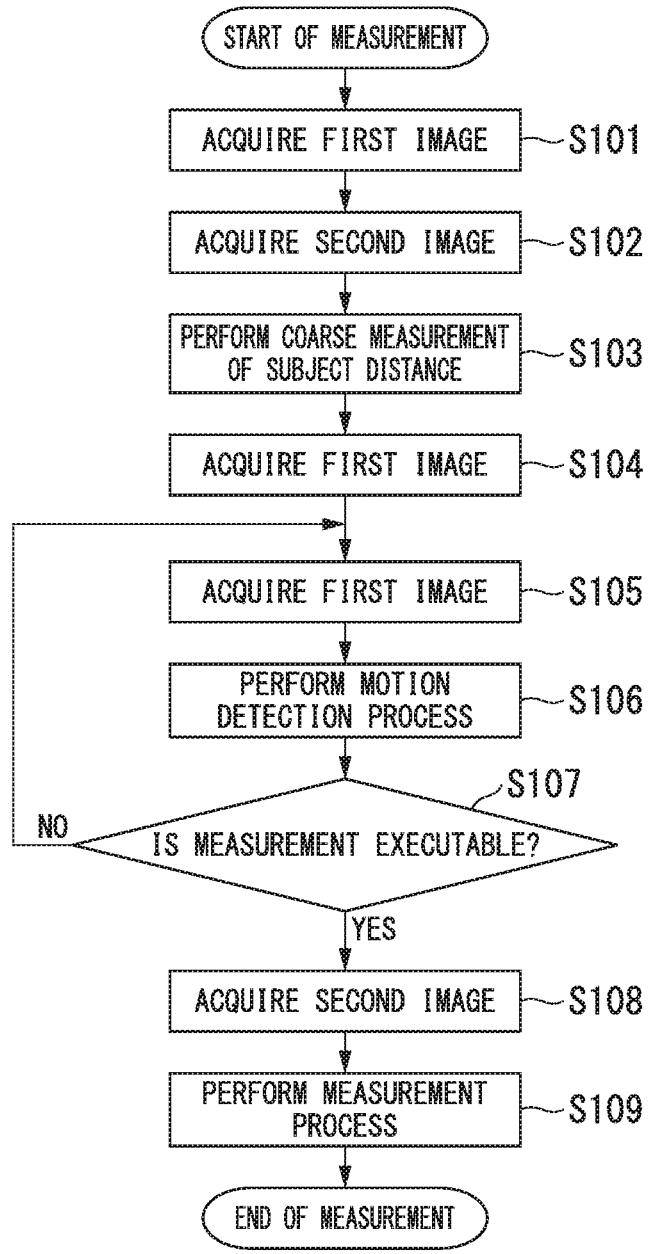
FIG. 3 is a flowchart showing a measurement procedure in the first embodiment of the present invention.

FIG. 3 shows a measurement procedure in the first embodiment. Details of the measurement will be described with reference to FIG. 3.

After the measurement is started, the optical path switching unit 102 sets the optical path to the first optical path. Thereby, a first subject image based on light passing through the first objective optical system 100 is formed on the surface of the imaging element 104. The imaging element 104 captures the first subject image and generates a first image based on the first subject image. A timing at which the first subject image is captured is a first timing. The first image generated by the imaging element 104 is stored in the frame memory 107 (step S101).

After step S101, the optical path switching unit 102 sets the optical path to the second optical path. Thereby, a second subject image based on light passing through the second objective optical system 101 is formed on the surface of the imaging element 104. The imaging element 104 captures the second subject image and generates a second image based on the second subject image. A timing at which the second subject image is captured is a second timing. The second image generated by the imaging element 104 is stored in the frame memory 107 (step S102).

After step S102, the subject distance detection unit 108 reads the first image and the second image from the frame memory 107. The subject distance detection unit 108 performs coarse measurement of the subject distance. That is, the subject distance detection unit 108 detects the subject distance by stereo measurement using the first image and the second image (step S103). In many cases, a motion occurs between the imaging timings of the first image and the second image. However, in step S103, the subject distance detection unit 108 measures the subject distance without correcting the motion.

After step S103, processing similar to that of step S101 is performed. That is, the first image is acquired (step S104).

After step S104, processing similar to that of step S101 is performed. In other words, the first image is acquired (step S105).

After step S105, the motion detection unit 109 executes a motion detection process. That is, the motion detection unit 109 detects an amount of motion of the imaging element 104 by calculating an amount of displacement between a plurality of first images (step S106). When the processing of step S106 is initially executed, first images which are a calculation target of the amount of displacement are two first images generated in the processing of steps S104 and S105. Thereafter, when the processing of step S106 is executed, the first images which are the calculation target of the amount of displacement are two first images generated in the processing of step S105 performed two consecutive times.

After step S106, the measurement availability determination unit 110 reads the table from the frame memory 107. The measurement availability determination unit 110 acquires an allowable threshold value corresponding to the subject distance measured in step S103 from the table. The measurement availability determination unit 110 executes a measurement availability determination. That is, the measurement availability determination unit 110 determines whether or not measurement is executable by comparing the amount of motion detected in step S106 with the allowable threshold value (step S107).

In step S107, when the amount of motion is greater than the allowable threshold value, the measurement availability determination unit 110 determines that it is not possible to execute measurement. In this case, the processing of step S105 is executed. In step S107, when the amount of motion is less than the allowable threshold value, the measurement availability determination unit 110 determines that it is possible to execute measurement. In this case, processing similar to that of step S102 is performed. In other words, the second image is acquired (step S108).

After step S108, the measurement processing unit 111 reads the first image acquired in step S105 and the second image acquired in step S108 from the frame memory 107. When the processing of step S105 was executed a plurality of times, the measurement processing unit 111 reads the last acquired first image among the plurality of first images stored in the frame memory 107 from the frame memory 107. The measurement processing unit 111 executes a measurement process on the basis of the first image and the second image and outputs a measurement result to the control unit 106 (step S109). By performing the processing of step S109, the measurement is completed.

Details of the coarse measurement of the subject distance in step S103 will be described. In step S103, the first image and the second image are input to the subject distance detection unit 108, and the subject distance detection unit 108 detects the subject distance.

FIGS. 4A, 4B, 5A and 5B show examples of measurement points for measuring the subject distance. In order to speed up the processing, the subject distance is measured only at measurement points set on the image. One or more measurement points are set in the first image or the second image. An example in which a plurality of measurement points are set in the first image will be described below.

Figure 4A:
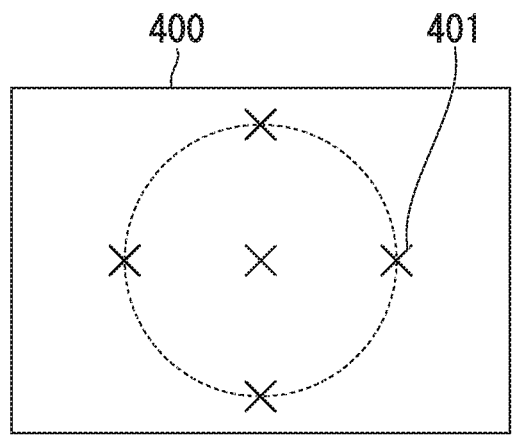
FIG. 4A is a diagram showing measurement points for measuring a subject distance in the first embodiment of the present invention.
Figure 4B:
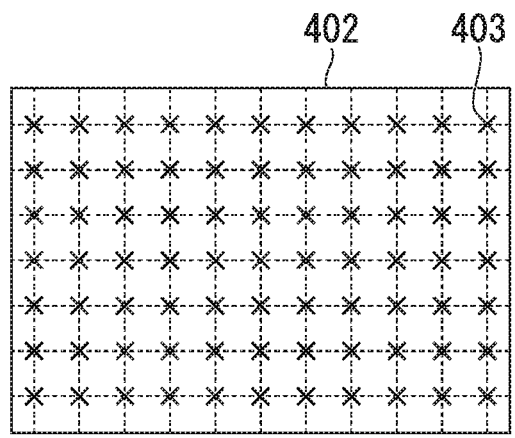
FIG. 4B is a diagram showing measurement points for measuring a subject distance in the first embodiment of the present invention.

In FIG. 4A, five measurement points 401 are set at the center of a first image 400. In FIG. 4B, a large number of measurement points 403 are set in a grid pattern in a first image 402.

Figure 5A:
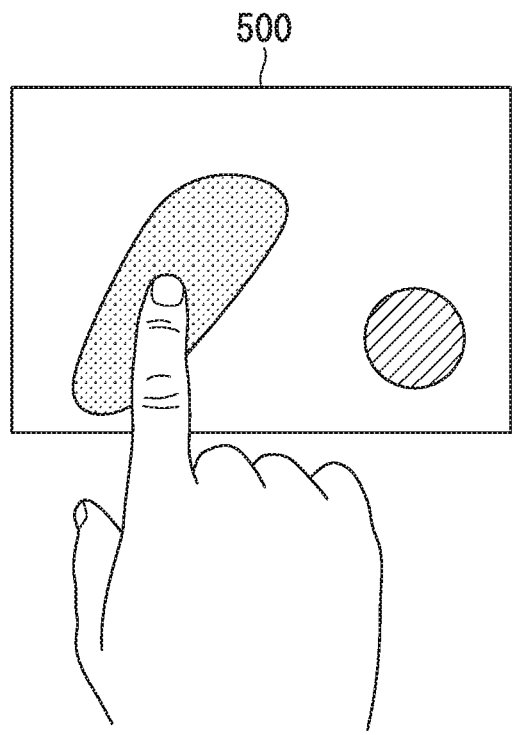
FIG. 5A is a diagram showing measurement points for measuring a subject distance in the first embodiment of the present invention.
Figure 5B:
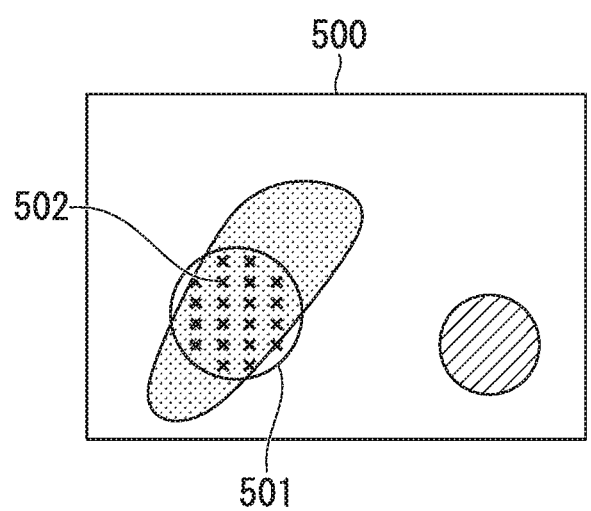
FIG. 5B is a diagram showing measurement points for measuring a subject distance in the first embodiment of the present invention.

FIG. 5A shows an example in which the user specifies a region where measurement points are set through a touch panel. An example in which the measurement device 10 has the touch panel will be described. The user touches a region desired to be measured in a first image 500 displayed on the touch panel. FIG. 5B shows a region 501 and a measurement point 502 specified by the user. The region 501 is specified at a position touched by the user on the touch panel. A large number of measurement points 502 are set inside the region 501.

Hereinafter, an example in which a measurement point 403 shown in FIG. 4B is set will be described. The subject distance detection unit 108 calculates the subject distance by stereo measurement at each measurement point set as described above. Details of the subject distance calculation process will be described with reference to FIG. 6.

Figure 6:
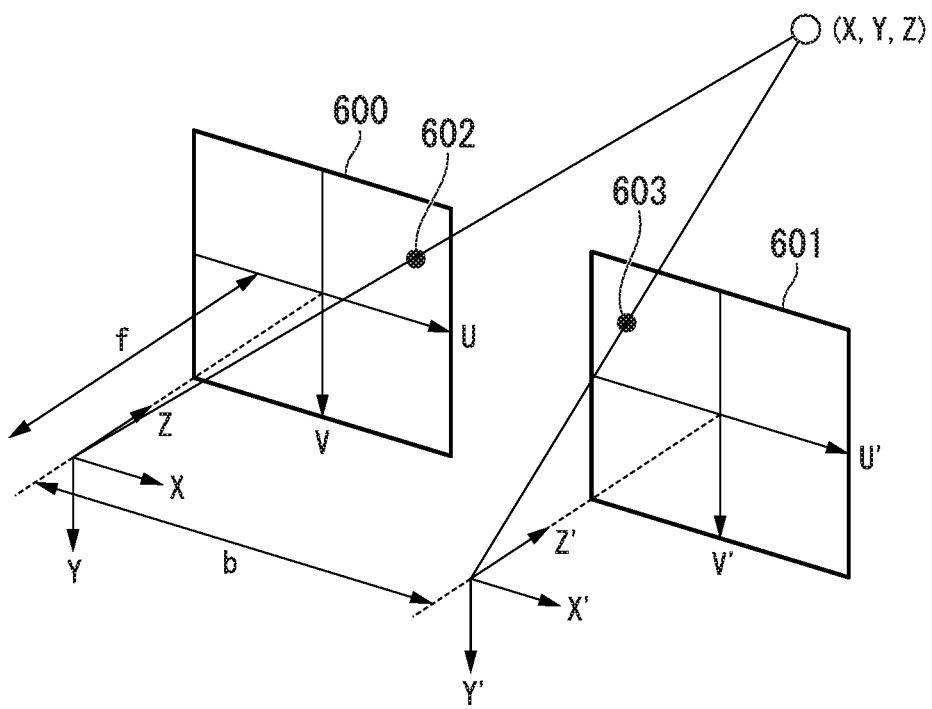
FIG. 6 is a diagram showing a process of calculating a subject distance in the first embodiment of the present invention.

A position of an object to be measured is (X, Y, Z). In FIG. 6, an XYZ coordinate system and an X'Y'Z' coordinate system are shown. The XYZ coordinate system is a coordinate system whose origin is an optical center of the first objective optical system 100. The X'Y'Z' coordinate system is a coordinate system whose origin is an optical center of the second objective optical system 101. A position of the subject is shown as coordinates in the XYZ coordinate system. Coordinates of a measurement point 602 in a UV coordinate system whose origin is a center of a first image 600 are (u, v). A position of the measurement point 603 in a U'V' coordinate system whose origin is a center of a second image 601 is (u', v'). The subject distance detection unit 108 performs stereo measurement using the first image 600 and the second image 601.

An amount of parallax d is given by Equation (1). For example, the amount of parallax d is given as the number of pixels.

$$D = u - u' \tag{1}$$

As in normal stereo measurement, the subject distance detection unit 108 can obtain physical coordinates of any measurement point by using Equations (2), (3), and (4) based on the principle of triangulation. In the following equations, b is a baseline length, i.e., a distance between the optical center of the first objective optical system 100 and the optical center of the second objective optical system 101. f is a focal length. δ is a pixel size of the imaging element 104. The calculated value of Z indicates the subject distance.

$$X = \frac{bu}{u - u'} = \frac{bu}{d} \tag{2}$$

$$Y = \frac{bv}{u - u'} = \frac{bv}{d} \tag{3}$$

$$Z = \frac{f}{\delta} \frac{b}{u - u'} = \frac{f \cdot b}{\delta \cdot d} \tag{4}$$

The subject distance detection unit 108 obtains correspondence relationships between measurement points of the first image and the second image by an image alignment and a correspondence point matching method which are well-known. In the following, an example in which template matching is used will be described. When correspondence relationships between the measurement points of each image are obtained through template matching, it may not necessarily be possible to uniquely obtain correspondence relationships at all measurement points. In a low contrast region where there are no alignment cues, a region where the same pattern is repeated, or the like, a reliability of a result of obtaining the correspondence relationship between the measurement points is low. Thus, the subject distance detection unit 108 may evaluate a reliability of each measurement point by using a well-known technique. For example, a technique of calculating the reliability of measurement points is disclosed in Japanese Patent No. 5744614. The subject distance detection unit 108 determines that the detection of the subject distance has succeeded at a measurement point with high reliability. The subject distance detection unit 108 determines that the detection of the subject distance has failed at a measurement point with low reliability.

Figure 7:
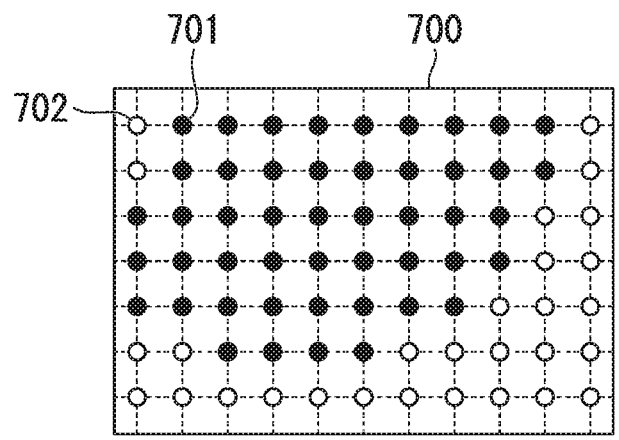
FIG. 7 is a diagram showing a result of detecting a subject distance at each measurement point in the first embodiment of the present invention.

FIG. 7 shows an example of a result of detecting the subject distance at each of measurement points. A measurement point 701 indicated by a black circle in a first image 700 is a measurement point at which detection of the subject distance has succeeded, i.e., at which the reliability is high. A measurement point 702 indicated by a white circle in the first image 700 is a measurement point at which the detection of the subject distance has failed, i.e., at which the reliability is low.

The subject distance detection unit 108 determines a representative subject distance on the basis of subject distances detected at a plurality of measurement points 701 with high reliability. For example, a representative subject distance is a median value or an average value of a plurality of subject distances. Alternatively, the representative subject distance is the farthest distance.

Details of the motion detection process in step S106 will be described. In step S106, two temporally consecutive first images are input to the motion detection unit 109, and the motion detection unit 109 detects an amount of deviation between the two first images as an amount of motion. The amount of deviation between the first images is related to the amount of motion in the translation direction of the scope 120. That is, the deviation between the first images decreases when the movement of the scope 120 in the translation direction is small, and the deviation between the first images increases when the motion of the scope 120 in the translation direction is large. Step S106 has an aim of detecting a magnitude of the motion of the scope 120 in the translation direction as the amount of motion of the imaging element 104.

Figure 8:
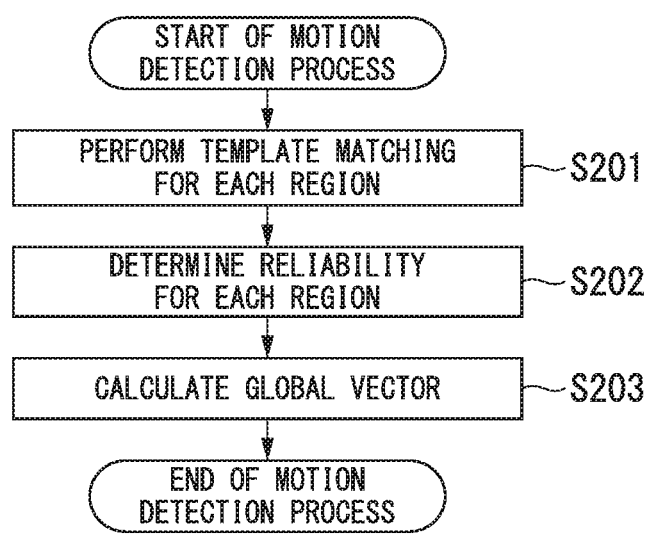
FIG. 8 is a flowchart showing a procedure of a motion detection process in the first embodiment of the present invention.

FIG. 8 shows a procedure of the motion detection process in step S106. Details of the motion detection process will be described with reference to FIG. 8.

Two temporally consecutive first images are input to the motion detection unit 109. The motion detection unit 109 performs template matching for each region by using the two input first images (step S201).

Figure 9A:
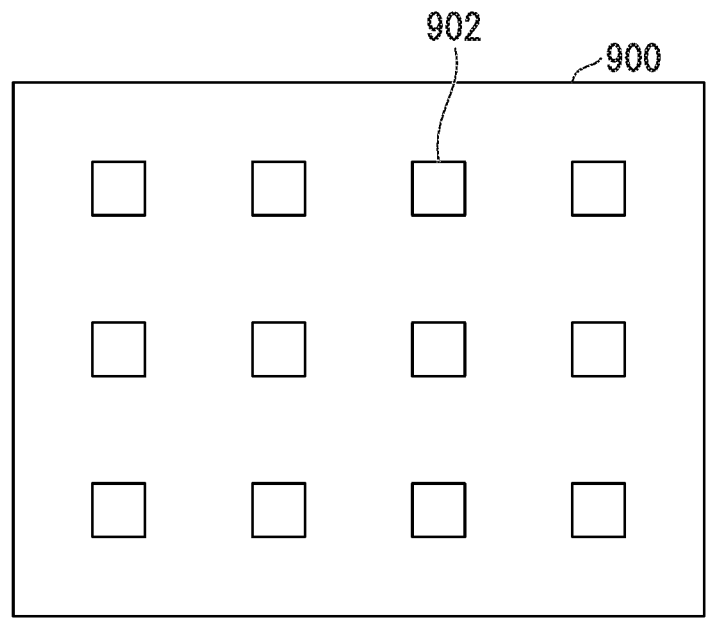
FIG. 9A is a diagram showing an image to be used for the motion detection process in the first embodiment of the present invention.
Figure 9B:
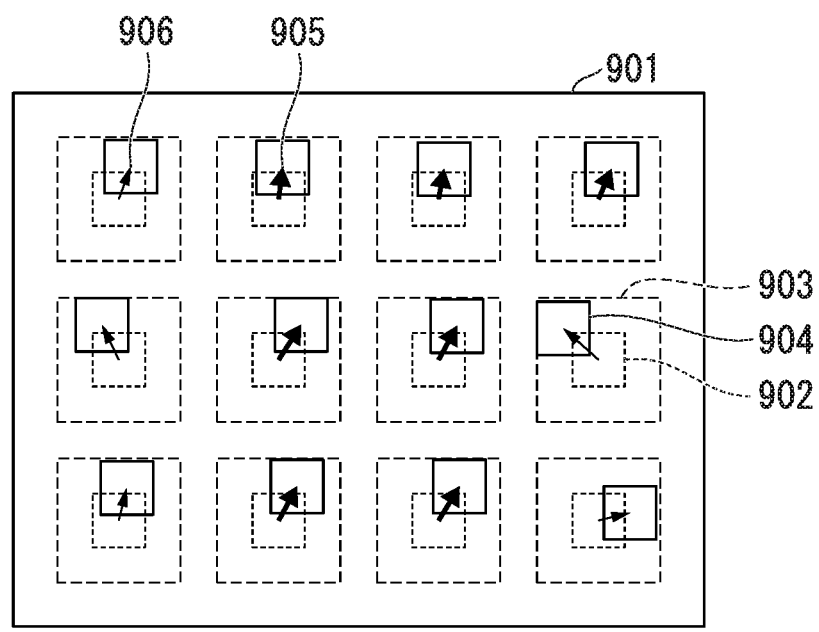
FIG. 9B is a diagram showing an image to be used for the motion detection process in the first embodiment of the present invention.

Details of the processing of step S201 will be described with reference to FIGS. 9A and 9B. A first image generated earlier is a reference image 900 (FIG. 9A) and a first image generated later is an alignment image 901 (FIG. 9B). The first image generated later may be the reference image 900 and the first image generated earlier may be the alignment image 901.

Template regions 902 are arranged at regular intervals in the reference image 900. The motion detection unit 109 searches for a region matching an image within the template region 902 in the alignment image 901. A matching search range 903 within a certain range centered on a position of the template region 902 of the reference image 900 is set in the alignment image 901. The motion detection unit 109 calculates a matching position 904 in the matching search range 903 in which a degree of matching between the matching search range 903 in the alignment image 901 and the template area 902 in the reference image 900 is highest. Well-known indices such as a sum of squared differences (SSD), a sum of absolute differences (SAD), a normalized cross correlation (NCC) and a zero means normalized cross correlation (ZNCC) can be used as indices indicating the degree of matching.

In step S201, the motion detection unit 109 calculates a displacement between a matching position 904 in the alignment image 901 and a position of each template region 902 of the reference image 900 as a movement vector of each template region 902. In a template matching process, when there is a cue from which a correspondence point is uniquely obtained, a movement vector with high reliability can be calculated. However, the reliability of the motion vector is low in a low contrast region, a repetitive pattern region, or the like where there are no alignment cues. After step S201, the motion detection unit 109 determines the reliability of the movement vector of each template region 902 (step S202).

As a method for determining the reliability of the movement vector, for example, a known technique such as a technique disclosed in Japanese Patent No. 5744614 can be used. For example, the reliability of a movement vector 905 in FIG. 9B is high and the reliability of a movement vector 906 is low. After step S202, the motion detection unit 109 calculates a global vector by calculating an average of high-reliability movement vectors calculated in step S202 among movement vectors calculated in step S201 (step S203). At this time, the motion detection unit 109 may calculate the global vector from only the movement vectors of the region in the center of the image. Alternatively, the motion detection unit 109 may calculate the global vector by using a reliability value as a weight to calculate a weighted average. A magnitude of the global vector indicates an amount of displacement between two first images, i.e., an amount of motion. A direction of the global vector indicates a direction of displacement between the two first images, i.e., a motion direction. By performing the processing of step S203, the motion detection process is completed.

Details of the measurement availability determination in step S107 will be described. In step S107, results of detecting a subject distance and an amount of displacement between the first images are input to the measurement availability determination unit 110, and the measurement availability determination unit 110 determines whether or not measurement is executable. The amount of displacement between the first images is an amount of motion of the imaging element 104.

The influence of a translational motion of the scope 120 on parallax will be described. When a translational motion is superimposed on the scope 120 which is continuously performing imaging, a baseline length b changes to (b+Δb). An amount of parallax change Δd, which is an influence of an amount of change Δb of the baseline length b on the parallax, is given by Equation (5) obtained from Equation (4).

$$\Delta d = \frac{f \cdot \Delta b}{\delta \cdot Z} \quad (5)$$

A case in which the amount of change Δb of the baseline length b is constant, i.e., a case in which the same translational motion always occurs between timings at which two consecutive first images are acquired, will be described as an example. When the subject distance Z is short, the amount of parallax change Δd, i.e., the amount of motion, increases. When the subject distance Z is long, the amount of parallax change Δd, i.e., the amount of motion, decreases. Therefore, in the determination using a certain threshold value with respect to the amount of motion, a frequency at which the amount of motion settles within the allowable threshold value decreases when the subject distance Z is short. As a result, there is a problem that measurement may not be able to be started for a long time.

The influence of the amount of parallax change Δd caused by the translational motion of the scope 120 on subject distance measurement accuracy is expressed by Equation (6) using an error rate ErrorRate(Z) of the subject distance. Equation (6) indicates a ratio of an amount of subject distance change (Z'−Z) to the subject distance Z.

$$ErrorRate(Z) = \frac{Z'-Z}{Z} = \left(\frac{fb}{\delta(d+\Delta d)} - \frac{fb}{\delta d}\right)\frac{\delta d}{fb} = -\frac{\Delta d}{d+\Delta d} \quad (6)$$

When translational motion occurs, an amount of parallax change Δd occurs and the baseline length b changes to (b+Δb) in reality. The baseline length b is treated as a fixed parameter. Thus, an error in a depth direction due to a change in the subject distance from Z to Z' occurs.

As indicated by Equation (4), the subject distance Z and the amount of parallax d are inversely proportional to each other. Because the amount of parallax d increases as the subject distance Z decreases, the influence of the amount of parallax change Δd, i.e., the amount of motion, on the subject distance measurement accuracy becomes small. On the other hand, because the amount of parallax d decreases when the subject distance Z becomes longer, the amount of parallax change Δd, i.e., the amount of motion, has a larger influence on the subject distance measurement accuracy.

Therefore, by setting a large allowable threshold value when the subject distance Z is short and setting a small allowable threshold value when the subject distance Z is long, it is possible to secure the measurement accuracy and increase the execution frequency of measurement. The measurement accuracy to be secured is the accuracy of a result of measuring the subject shape and the subject distance. Using this principle, a table in which subject distances and allowable threshold values are associated is generated.

A method for generating a table in which subject distances and allowable threshold values are associated will be described. A relationship between the amount of parallax change Δd and the subject distance Z is given by Equation (7) according to Equations (4), (5) and (6).

$$\Delta d = -\frac{ErrorRate(Z)}{ErrorRate(Z)+1} \cdot \frac{fb}{\delta Z} \quad (7)$$

An allowable value of the amount of parallax change Δd can be determined for each subject distance Z by prescribing the allowable error rate ErrorRate(Z) of the subject distance for each subject distance Z as a specification, i.e., by setting the allowable error rate ErrorRate(Z) to a constant. Therefore, it is possible to generate in advance a table in which subject distances and allowable threshold values are associated.

FIG. 10 shows an example of a table in which subject distances and allowable threshold values are associated. An allowable threshold value of 1.0 pixel is associated with a subject distance of 10 mm or less. When the subject distance detected by the subject distance detection unit 108 is 10 mm or less, the execution of measurement is allowed if the amount of displacement between the first images, i.e., the amount of motion, is less than 1.0 pixel. A subject distance greater than 10 mm and less than or equal to 20 mm is associated with an allowable threshold value of 0.5 pixels. When the subject distance detected by the subject distance detection unit 108 is greater than 10 mm and less than or equal to 20 mm, the execution of measurement is allowed if the amount of displacement between the first images, i.e., the amount of motion, is less than 0.5 pixels.

A subject distance greater than 20 mm and less than or equal to 30 mm is associated with an allowable threshold value of 0.3 pixels. When the subject distance detected by the subject distance detection unit 108 is greater than 20 mm and less than or equal to 30 mm, the execution of measurement is allowed if the amount of displacement between the first images, i.e., the amount of motion, is less than 0.3 pixels. A subject distance greater than 30 mm and less than or equal to 40 mm is associated with an allowable threshold value of 0.2 pixels. When the subject distance detected by the subject distance detection unit 108 is greater than 30 mm and less than or equal to 40 mm, the execution of measurement is allowed if the amount of displacement between the first images, i.e., the amount of motion, is less than 0.2 pixels.

A subject distance greater than 40 mm and less than or equal to 50 mm is associated with an allowable threshold value of 0.2 pixels. When the subject distance detected by the subject distance detection unit 108 is greater than 40 mm and less than or equal to 50 mm, the execution of measurement is allowed if the amount of displacement between the first images, i.e., the amount of motion, is less than 0.2 pixels. An allowable threshold value of 0.2 pixels is associated with the subject distance greater than 50 mm. When the subject distance detected by the subject distance detection unit 108 is greater than 50 mm, the execution of measurement is allowed if the amount of displacement between the first images, i.e., the amount of motion, is less than 0.2 pixels. Details of the table are not limited to the above example.

As shown in FIG. 10, a first allowable threshold value corresponding to a first subject distance is greater than a second allowable threshold value corresponding to a second subject distance greater than the first subject distance.

A method for determining whether or not measurement is possible using the table shown in FIG. 10 will be described. The measurement availability determination unit 110 acquires an allowable threshold value corresponding to the subject distance measured in step S103 from the table shown in FIG. 10. When the amount of motion detected in step S106 is less than the allowable threshold value, the measurement availability determination unit 110 determines that it is possible to execute measurement. When the amount of motion detected in step S106 is greater than the allowable threshold value, the measurement availability determination unit 110 determines that it is not possible to execute measurement.

Details of the measurement process in step S109 will be described. In step S109, the first image and the second image are input to the measurement processing unit 111, and the measurement processing unit 111 executes the measurement process. The measurement processing unit 111 outputs a measurement result. The measurement result is at least one of a subject shape and a subject distance.

Figure 11A:
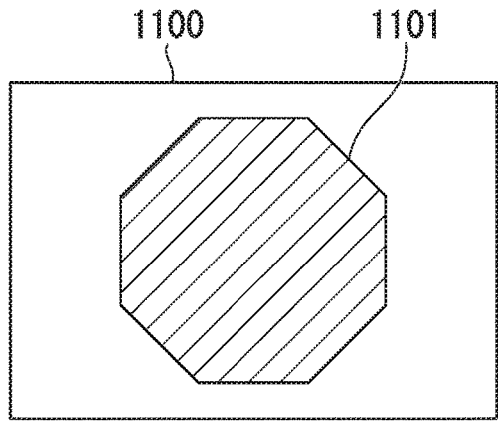
FIG. 11A is a diagram showing a measurement region serving as a target of a measurement process in the first embodiment of the present invention.
Figure 11B:
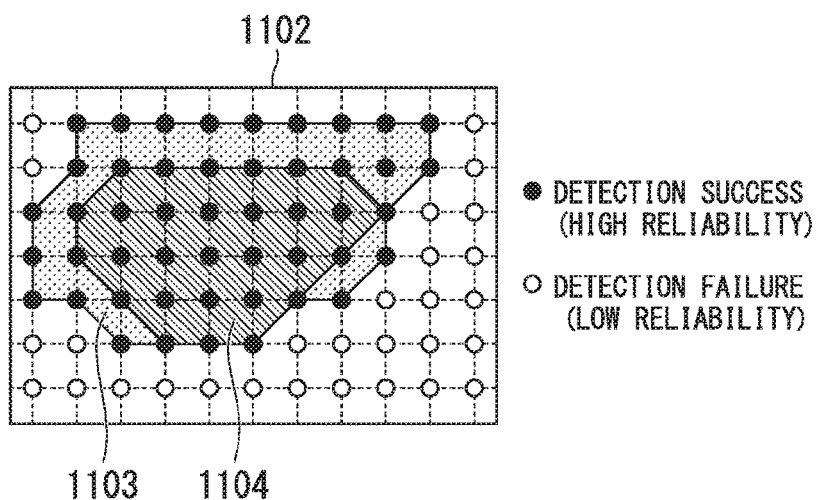
FIG. 11B is a diagram showing a measurement region serving as a target of a measurement process in the first embodiment of the present invention.

FIGS. 11A and 11B show an example of a measurement region to be subjected to the measurement process. In FIG. 11A, measurement is performed within a predetermined region 1101 in a first image 1100. In FIG. 11B, measurement is performed within a second region 1104 included in a first region 1103 in a first image 1102. The first region 1103 is a region including a measurement point with high reliability at which detection of the subject distance has succeeded in coarse measurement of the subject distance (step S103). The second region 1104 is a region where the amount of motion detected at each measurement point is less than the allowable threshold value.

Specific details of the measurement process are a stereo measurement process. A basic principle thereof is the same as the principle described with respect to the coarse measurement of subject processing in step S103. The measurement processing unit 111 calculates a subject distance Z. Alternatively, the measurement processing unit 111 calculates three-dimensional coordinates (X, Y, Z) of each measurement point and calculates a subject shape by using three-dimensional coordinates of a plurality of measurement points.

After the measurement process, the measurement processing unit 111 may calculate the reliability of measurement shown in Equation (8). In Equation (8), $\Delta b$ denotes an amount of displacement between first images in a measurement region, i.e., an amount of motion. $b_{th}(Z)$ is an allowable threshold value determined for each subject distance. As indicated by Equation (8), the reliability of measurement is a ratio of the amount of motion to the allowable threshold value.

$$\text{reliability} = \frac{\Delta b}{b_{th}(Z)} \qquad (8)$$

Figure 12:
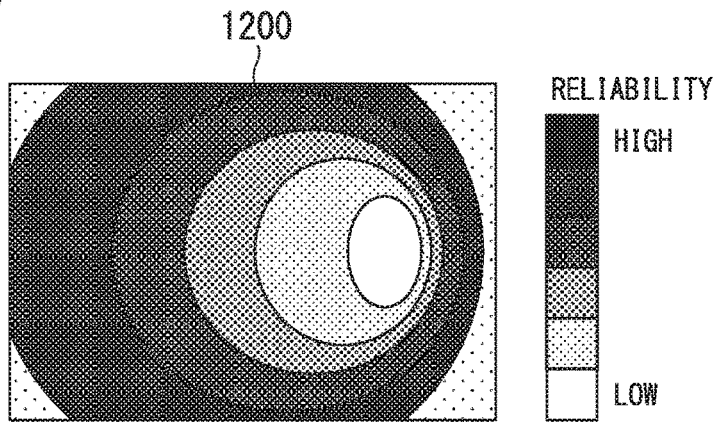
FIG. 12 is a diagram showing a reliability distribution in the first embodiment of the present invention.

When the measurement device 10 has a display, the reliability calculated by Equation (8) may be displayed on the display. FIG. 12 shows an example of a reliability distribution 1200 displayed on the display. The reliability at the measurement point set in the coarse measurement of the subject distance (step S103) is calculated by Equation (8). The reliability distribution 1200 visually indicates the reliability at each measurement point. A user can determine validity of the measurement result by checking the reliability of the measurement point set in the measurement process (step S109) on the reliability distribution 1200.

As described above, the measurement device 10 acquires an image while performing switching between the first optical path and the second optical path and measures a subject by the principle of stereo measurement. A large allowance amount for the amount of motion is set in a subject region of a short distance where a motion of the imaging element 104 is likely to occur and a motion hardly affects the measurement accuracy. A small allowance amount for the amount of motion is set in a subject region of a long distance where a motion of the imaging element 104 is unlikely to occur, but a motion easily affects the measurement accuracy. Thereby, the measurement device 10 can secure a desired measurement accuracy and increase a frequency of execution of measurement.

First Modified Example of First Embodiment

In a first modified example of the first embodiment, a frame memory 107 does not need to store a table in which subject distances and allowable threshold values are associated. On the basis of an amount of errors in a result of a measurement process, a measurement availability determination unit 110 calculates an allowable threshold value corresponding to the subject distance detected by a subject distance detection unit 108. The amount of errors of the result of the measurement process is predetermined for each subject distance.

An allowable error rate ErrorRate(Z) of a subject distance for each subject distance Z is predetermined as a specification, i.e., the allowable error rate ErrorRate(Z) is set to a constant. In step S107 shown in FIG. 3, the measurement availability determination unit 110 calculates an allowable threshold value of an amount of parallax change $\Delta d$ for each subject distance Z detected in step S103 by Equation (7). The measurement availability determination unit 110 determines whether or not measurement is executable by comparing the amount of motion detected in step S106 with the calculated allowable threshold value.

As described above, the measurement availability determination unit 110 calculates an allowable threshold value corresponding to the subject distance for each determination of measurement availability. Thus, the frame memory 107 does not need to store a table in which subject distances and allowable threshold values are associated.

Second Modified Example of First Embodiment

In the first embodiment, acquisition of a first image (step S101) and acquisition of a second image (step S102) are performed before coarse measurement of a subject distance (step S103), and these images are used for the coarse measurement of the subject distance (step S103). When an extremely large motion occurs in an imaging element 104 between the acquisition of the first image (step S101) and the acquisition of the second image (step S102), it is difficult to obtain a correct subject distance.

A second modified example of the first embodiment solves this problem. The second image is acquired only when a magnitude of an amount of displacement between first images is less than a predetermined threshold value.

Figure 13:
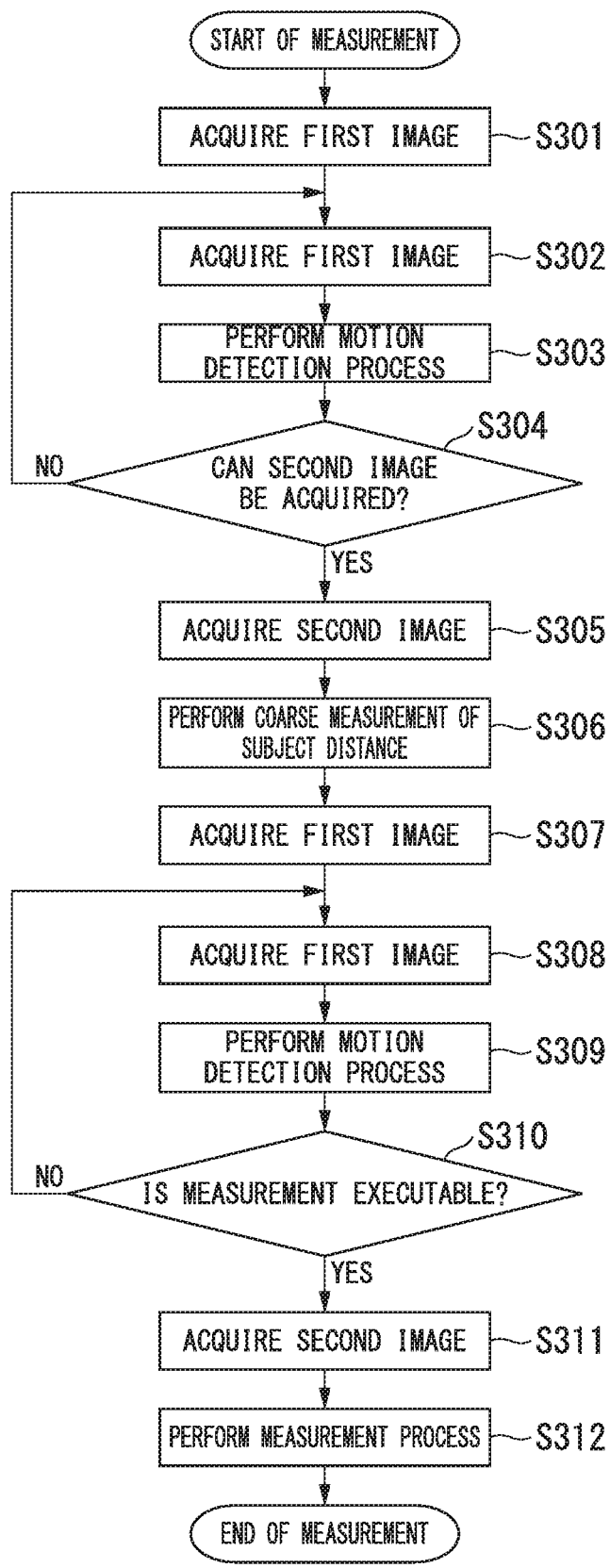
FIG. 13 is a flowchart showing a measurement procedure in a second modified example of the first embodiment of the present invention.

FIG. 13 shows a measurement procedure in the second modified example of the first embodiment. Details of the measurement in the second modified example of the first embodiment will be described with reference to FIG. 13.

After the measurement is started, the first image is acquired (step S301). The processing of step S301 is similar to the processing of step S101 shown in FIG. 3.

After step S301, processing similar to the processing of step S301 is performed. That is, the first image is acquired (step S302).

After step S302, a motion detection unit 109 executes a motion detection process (step S303). The processing of step S303 is similar to the processing of step S106 shown in FIG. 3.

After step S303, a control unit 106 compares an amount of displacement between the first images detected in step S303, i.e., an amount of motion of the imaging element 104, with a predetermined threshold value. Thereby, the control unit 106 determines whether or not the second image can be acquired (step S304). A threshold value to be used for the determination in step S304 is independent of the allowable threshold value in the table shown in FIG. 10.

In step S304, when the amount of motion is greater than the threshold value, the control unit 106 determines that the second image cannot be acquired. In this case, the processing of step S302 is executed. In step S304, when the amount of motion is less than the threshold value, the control unit 106 determines that the second image can be acquired. In this case, the second image is acquired (step S305). The processing of steps S305 to S312 is similar to the processing of steps S102 to S109 shown in FIG. 3.

In the process shown in FIG. 13, only when the amount of motion detected in step S303 is less than a predetermined threshold value, the second image is acquired in step S305. Thus, the robustness to a motion of the imaging element 104 is improved.

Second Embodiment

In the first embodiment, an allowable threshold value according to the subject distance is used for determining measurement availability. On the other hand, in the second embodiment, an allowable threshold value according to an amount of parallax between a first image and a second image is used for determining measurement availability.

Figure 14:
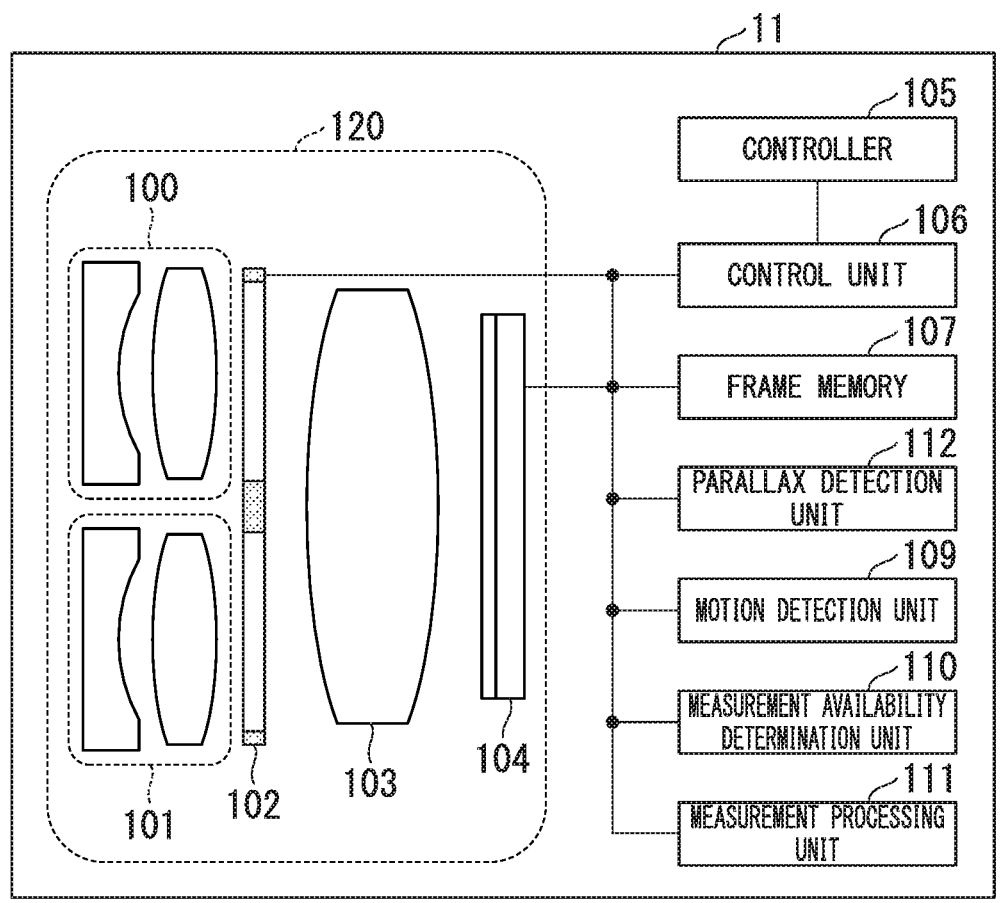
FIG. 14 is a block diagram showing a configuration of a measurement device according to a second embodiment of the present invention.

FIG. 14 shows a configuration of a measurement device 11 according to the second embodiment of the present invention. Differences from the configuration shown in FIG. 1 will be described with respect to the configuration shown in FIG. 14.

The measurement device 11 includes a parallax detection unit 112 instead of the subject distance detection unit 108 in the measurement device 10 shown in FIG. 1. The parallax detection unit 112 detects an amount of parallax between the first image and the second image. The parallax detection unit 112 may include at least one of a processor and a logic circuit. The parallax detection unit 112 can include one or more processors. The parallax detection unit 112 can include one or more logic circuits.

A measurement availability determination unit 110 determines whether or not the measurement is executable by comparing an amount of motion detected by a motion detection unit 109 with an allowable threshold value according to an amount of parallax detected by the parallax detection unit 112. A frame memory 107 stores a table in which the amount of motion and the allowable threshold value are associated.

Regarding points other than the above, the configuration shown in FIG. 14 is similar to the configuration shown in FIG. 1.

FIG. 15 shows a measurement procedure in the second embodiment. Details of measurement in the second embodiment will be described with reference to FIG. 15.

The processing of steps S401 and S402 is executed. The processing of steps S401 and S402 is similar to the processing of steps S101 and S102 shown in FIG. 3.

After step S402, the parallax detection unit 112 reads a first image and a second image from the frame memory 107. The parallax detection unit 112 detects an amount of parallax between the first image and the second image (step S403).

After step S403, the processing of steps S404 to S406 is executed. The processing of steps S404 to S406 is similar to the processing of steps S104 to S106 shown in FIG. 3.

After step S406, the measurement availability determination unit 110 reads the table from the frame memory 107. The measurement availability determination unit 110 acquires an allowable threshold value corresponding to the amount of parallax detected in step S403 from the table. The measurement availability determination unit 110 executes a measurement availability determination. That is, the measurement availability determination unit 110 determines whether or not measurement is executable by comparing an amount of motion detected in step S406 with the allowable threshold value (step S407).

In step S407, when the amount of motion is greater than the allowable threshold value, the measurement availability determination unit 110 determines that it is not possible to execute measurement. In this case, the processing of step S405 is executed.

In step S407, when the amount of motion is less than the allowable threshold value, the measurement availability determination unit 110 determines that it is possible to execute measurement. In this case, processing similar to the processing of step S402 is performed. That is, the second image is acquired (step S408).

After step S408, a measurement processing unit 111 executes a measurement process (step S409). The processing of step S409 is similar to the processing of step S109 shown in FIG. 3. By performing the processing of step S409, the measurement is completed.

Details of the measurement availability determination in step S407 will be described. In step S407, a result of detecting the amount of parallax and the amount of displacement between the first images are input to the measurement availability determination unit 110, and the measurement availability determination unit 110 determines whether or not measurement is executable. The amount of displacement between the first images is an amount of motion of an imaging element 104.

A relationship between an amount of parallax d and an amount of parallax change Δd is given by Equation (9) according to the above-described Equations (4), (5), and (6).

$$\Delta d = -\frac{ErrorRate(Z)}{ErrorRate(Z) + 1} \cdot d \tag{9}$$

An allowable value of the amount of parallax change Δd can be determined for each amount of parallax d by prescribing an allowable error rate ErrorRate(Z) of a subject distance as a specification for each amount of parallax d, i.e., by setting the allowable error rate ErrorRate(Z) to a constant. Therefore, a table in which amounts of parallax and allowable threshold values are associated can be generated in advance.

FIG. 16 shows an example of a table in which amounts of parallax and allowable threshold values are associated. An allowable threshold value of 0.2 pixels is associated with an amount of parallax of 10 pixels or less. When the amount of parallax detected by the parallax detection unit 112 is 10 pixels or less, the execution of measurement is allowed if the amount of displacement between the first images, i.e., the amount of motion, is less than 0.2 pixels. An allowable threshold value of 0.2 pixels is associated with an amount of parallax greater than 10 pixels and less than or equal to 20 pixels. When the amount of parallax detected by the parallax detection unit 112 is greater than 10 pixels and less than or equal to 20 pixels, the execution of measurement is allowed if the amount of displacement between the first images, i.e., the amount of motion, is less than 0.2 pixels.

An allowable threshold value of 0.2 pixels is associated with an amount of parallax greater than 20 pixels and less than or equal to 30 pixels. When the amount of parallax detected by the parallax detection unit 112 is greater than 20 pixels and is less than or equal to 30 pixels, the execution of measurement is allowed if the amount of displacement between the first images, i.e., the amount of motion, is less than 0.2 pixels. An allowable threshold value of 0.3 pixels is associated with an amount of parallax greater than 30 pixels and less than or equal to 40 pixels. When the amount of parallax detected by the parallax detection unit 112 is greater than 30 pixels and less than or equal to 40 pixels, the execution of measurement is allowed if the amount of displacement between the first images, i.e., the amount of motion, is less than 0.3 pixels.

An allowable threshold value of 0.5 pixels is associated with an amount of parallax greater than 40 pixels and less than or equal to 50 pixels. When the amount of parallax detected by the parallax detection unit 112 is greater than 40 pixels and less than or equal to 50 pixels, the execution of measurement is allowed if the amount of displacement between the first images, i.e., the amount of motion, is less than 0.5 pixels. An allowable threshold value of 1.0 pixel is associated with an amount of parallax greater than 50 pixels. When the amount of parallax detected by the parallax detection unit 112 is greater than 50 pixels, the execution of measurement is allowed if the amount of displacement between the first images, i.e., the amount of motion, is less than 1.0 pixel. Details of the table are not limited to the above example.

As shown in FIG. 16, a first allowable threshold value corresponding to a first amount of parallax is greater than a second allowable threshold value corresponding to a second amount of parallax less than the first amount of parallax.

A method for determining whether or not measurement is possible using the table shown in FIG. 16 will be described. The measurement availability determination unit 110 acquires an allowable threshold value corresponding to the amount of parallax detected in step S403 from the table shown in FIG. 16. When the amount of motion detected in step S406 is less than the allowable threshold value, the measurement availability determination unit 110 determines that it is possible to execute measurement. When the amount of motion detected in step S406 is greater than the allowable threshold value, the measurement availability determination unit 110 determines that it is not possible to execute measurement.

As described above, the measurement device 11 acquires an image while performing switching between a first optical path and a second optical path and measures a subject by the principle of stereo measurement. A large allowance amount for the amount of motion is set in a subject region of a short distance where a motion of the imaging element 104 is likely to occur and a motion hardly affects the measurement accuracy. A small allowance amount for the amount of motion is set in a subject region of a long distance where a motion of the imaging element 104 is unlikely to occur, but a motion easily affects the measurement accuracy. Thereby, the measurement device 11 can secure a desired measurement accuracy and increase a frequency of execution of measurement.

Modified Example of Second Embodiment

In a modified example of the second embodiment, a frame memory 107 does not need to store a table in which amounts of parallax and allowable threshold values are associated. A measurement availability determination unit 110 calculates an allowable threshold value corresponding to an amount of parallax detected by a parallax detection unit 112 on the basis of an amount of errors in a result of a measurement process. The amount of errors of the result of the measurement process is predetermined for each amount of parallax.

An allowable error rate ErrorRate(Z) of a subject distance for each amount of parallax d is predetermined as a specification, i.e., the allowable error rate ErrorRate(Z) is set to a constant. In step S407 shown in FIG. 15, the measurement availability determination unit 110 calculates an allowable threshold value of an amount of parallax change Δd for each amount of parallax d detected in step S403 by Equation (9). The measurement availability determination unit 110 determines whether or not the measurement is executable by comparing the amount of motion detected in step S406 with the calculated allowable threshold value.

As described above, the measurement availability determination unit 110 calculates an allowable threshold value corresponding to the amount of parallax for each determination of measurement availability. Thus, a frame memory 107 does not need to store a table in which amounts of parallax and allowable thresholds value are associated.

Third Embodiment

In the first embodiment, it is determined whether or not measurement is possible before the measurement process. On the other hand, in the third embodiment, after the measurement process, the validity of a measurement result is determined using a subject distance obtained in the measurement process.

Figure 17:
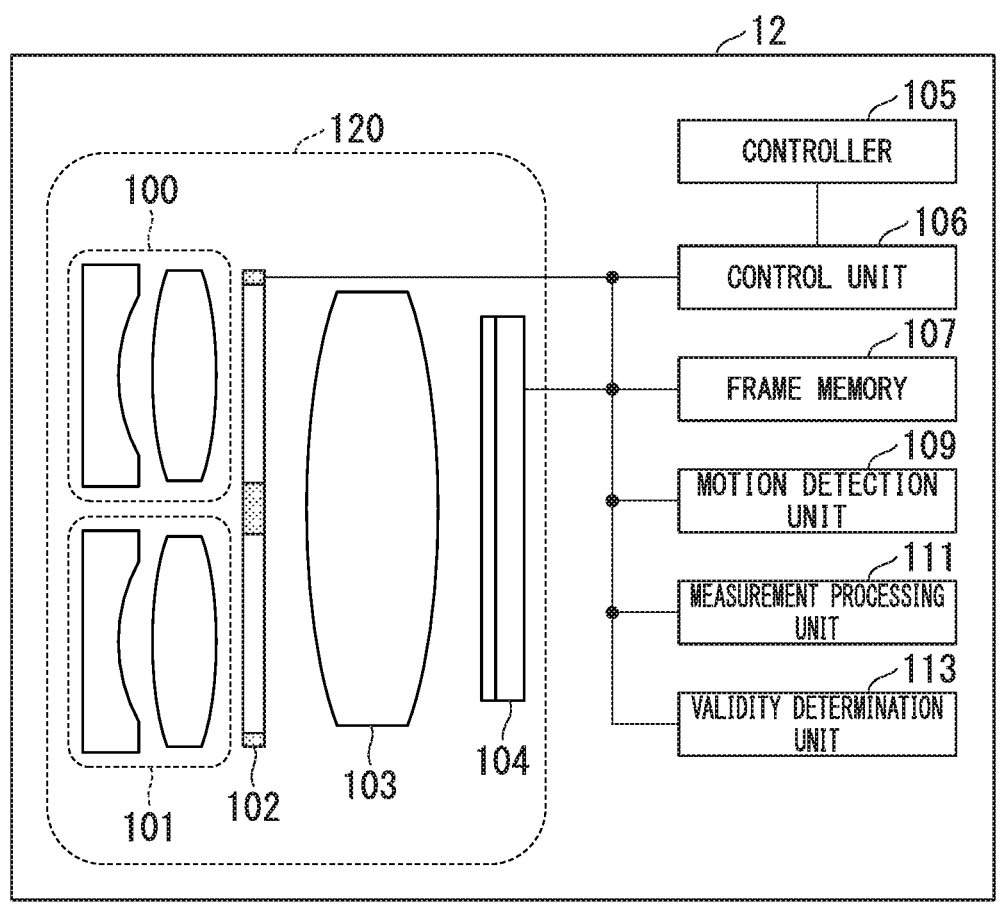
FIG. 17 is a block diagram showing a configuration of a measurement device according to a third embodiment of the present invention.

FIG. 17 shows a configuration of a measurement device 12 according to the third embodiment of the present invention. Differences from the configuration shown in FIG. 1 will be described with respect to the configuration shown in FIG. 17.

The measurement device 12 does not have the subject distance detection unit 108 in the measurement device 10 shown in FIG. 1. A measurement processing unit 111 executes a measurement process on the basis of a first image and a second image and detects a subject distance in the measurement process. When the measurement of a subject shape is the main purpose of the measurement process, the measurement processing unit 111 measures a subject distance in addition to the subject shape. The measurement device 12 has a validity determination unit 113 instead of the measurement availability determination unit 110 in the measurement device 10 shown in FIG. 1. The validity determination unit 113 determines the validity of a result of the measurement process by comparing an amount of motion detected by a motion detection unit 109 with an allowable threshold value according to the subject distance detected by the measurement processing unit 111. The validity determination unit 113 may include at least one of a processor and a logic circuit. The validity determination unit 113 can include one or more processors. The validity determination unit 113 can include one or more logic circuits.

Regarding points other than the above, the configuration shown in FIG. 17 is similar to the configuration shown in FIG. 1.

Figure 18:
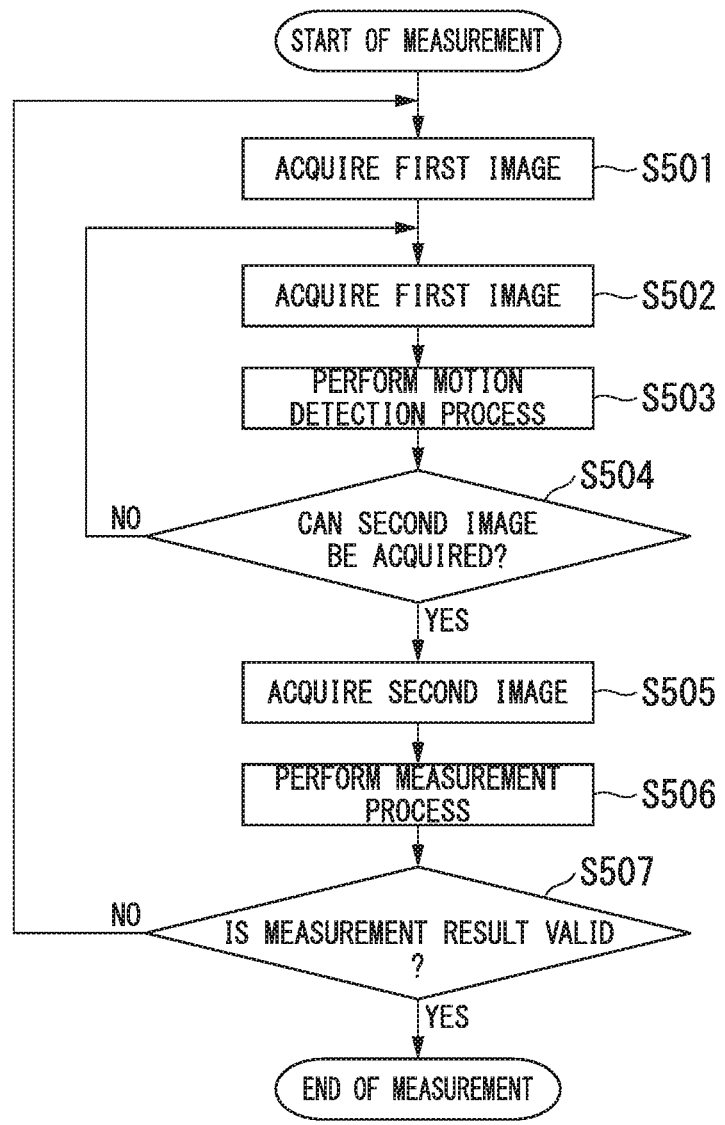
FIG. 18 is a flowchart showing a measurement procedure in the third embodiment of the present invention.

FIG. 18 shows a measurement procedure in the third embodiment. Details of the measurement in the third embodiment will be described with reference to FIG. 18.

The processing of steps S501 and S502 is executed. The processing of steps S501 and step S502 is similar to the processing of steps S101 and S102 shown in FIG. 3.

After step S502, the motion detection unit 109 executes a motion detection process (step S503). The processing of step S503 is similar to the processing of step S106 shown in FIG. 3.

After step S503, the control unit 106 compares an amount of displacement between first images detected in step S503, i.e., an amount of motion of an imaging element 104, with a predetermined threshold value. Thereby, the control unit 106 determines whether or not the second image can be acquired (step S504). The processing of step S504 is similar to the processing of step S304 shown in FIG. 13.

In step S504, when the amount of motion is greater than the threshold value, the control unit 106 determines that the second image cannot be acquired. In this case, the processing of step S502 is executed. In step S504, when the amount of motion is less than the threshold value, the control unit 106 determines that the second image can be acquired. In this case, the second image is acquired (step S505). The processing of step S505 is similar to the processing of step S108 shown in FIG. 3.

After step S505, the measurement processing unit 111 executes a measurement process on the basis of the first image and the second image and outputs a measurement result to the control unit 106 (step S506). In step S506, the measurement processing unit 111 measures a subject shape and a subject distance. In this case, the subject distance is measured during the measurement process. Alternatively, in step S506, the measurement processing unit 111 measures only the subject distance.

After step S506, the validity determination unit 113 reads a table from a frame memory 107. The validity determination unit 113 obtains an allowable threshold value corresponding to the subject distance measured in step S506 from the table. The validity determination unit 113 executes a validity determination. That is, the validity determination unit 113 determines the validity of the measurement result by comparing the amount of motion detected in step S503 with the allowable threshold value (step S507). In the determination of step S507, a table similar to the table shown in FIG. 10 is used.

In step S507, when the amount of motion is greater than the allowable threshold value, the validity determination unit 113 determines that the measurement result is not valid. In this case, the processing of step S501 is executed. In step S507, when the amount of motion is less than the allowable threshold value, the validity determination unit 113 determines that the measurement result is valid. In this case, the measurement is completed.

The threshold value used for the determination of step S504 may be a threshold value according to the subject distance. For example, when the processing of step S504 is initially executed, a predetermined initial value is used as the threshold value. In the subsequent processing of step S504, a threshold value according to the subject distance measured in step S506 is used. The processing of step S504 is not necessary.

As described above, the measurement device 12 acquires an image while performing switching between a first optical path and a second optical path and measures a subject by the principle of stereo measurement. A large allowance amount for the amount of motion is set in a subject region of a short distance where a motion of an imaging element 104 is likely to occur and a motion hardly affects the measurement accuracy. A small allowance amount for the amount of motion is set in a subject region of a long distance where a motion of the imaging element 104 is unlikely to occur, but a motion easily affects the measurement accuracy. Thereby, the measurement device 12 can secure a desired measurement accuracy and increase a frequency of execution of measurement. Also, because a processing system for detecting the subject distance need not be independent from the measurement processing unit 111, the processing system can be simplified.

Modified Example of Third Embodiment

In the modified example of the third embodiment, a frame memory 107 does not need to store a table in which subject distances and allowable threshold values are associated. A validity determination unit 113 calculates an allowable threshold value corresponding to a subject distance detected by a measurement processing unit 111 on the basis of an amount of errors in a result of a measurement process. The amount of errors of the result of the measurement process is predetermined for each subject distance.

An allowable error rate ErrorRate(Z) of a subject distance for each subject distance Z is predetermined as a specification, i.e., the allowable error rate ErrorRate(Z) is set to a constant. In step S507 shown in FIG. 18, the validity determination unit 113 calculates an allowable threshold value of an amount of parallax change Δd for each subject distance Z detected in step S506 by Equation (7). The validity determination unit 113 determines the validity of a measurement result by comparing the amount of motion detected in step S503 with the calculated allowable threshold value.

As described above, the validity determination unit 113 calculates an allowable threshold value corresponding to the subject distance every time the validity of the measurement result is determined. Thus, the frame memory 107 does not need to store a table in which subject distances and allowable threshold values are associated.

Fourth Embodiment

In the third embodiment, an allowable threshold value according to a subject distance is used for validity determination. On the other hand, in the fourth embodiment, an allowable threshold value according to an amount of parallax between a first image and a second image is used for a validity determination.

In the measurement device 12 shown in FIG. 17, a measurement processing unit 111 executes a measurement process on the basis of a first image and a second image, and detects parallax between the first image and the second image in the measurement process. A validity determination unit 113 determines the validity of a result of the measurement process by comparing the amount of motion detected by the motion detection unit 109 with the allowable threshold value according to the amount of parallax detected by the measurement processing unit 111.

Figure 19:
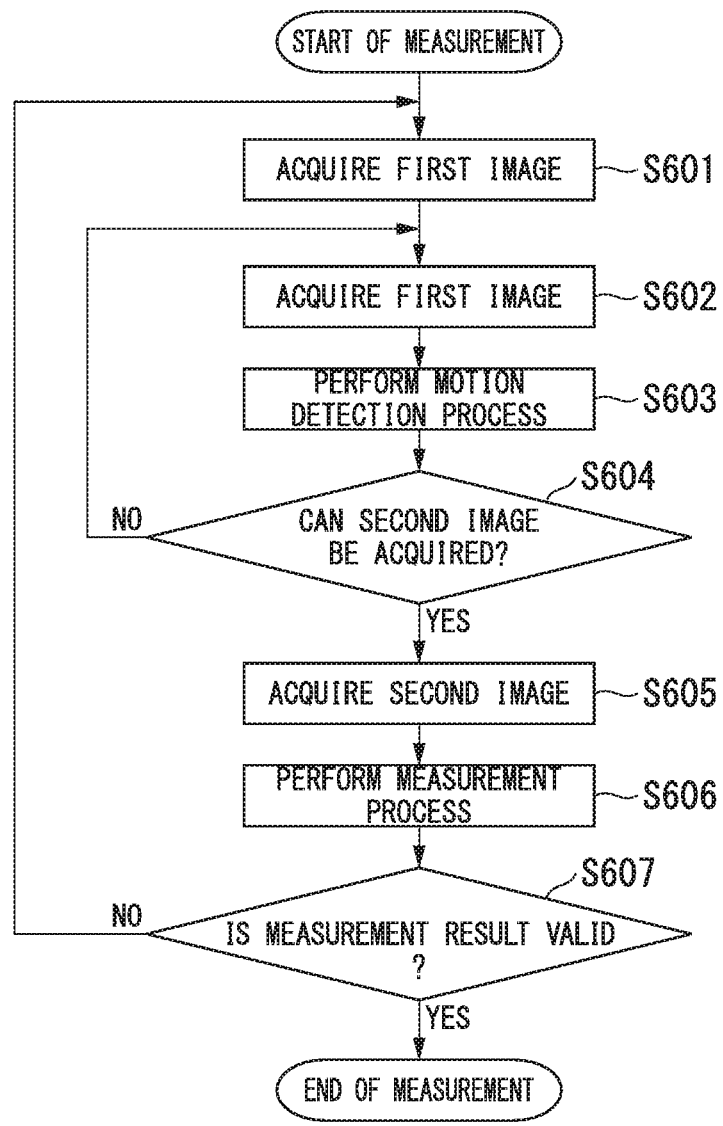
FIG. 19 is a flowchart showing a measurement procedure in a fourth embodiment of the present invention.

FIG. 19 shows a measurement procedure in the fourth embodiment. Details of measurement in the fourth embodiment will be described with reference to FIG. 19.

The processing of steps S601 and S602 is executed. The processing of steps S601 and S602 is similar to the processing of steps S101 and S102 shown in FIG. 3.

After step S602, a motion detection unit 109 executes a motion detection process (step S603). The processing of step S603 is similar to the processing of step S106 shown in FIG. 3.

After step S603, a control unit 106 compares an amount of displacement between first images detected in step S603, i.e., an amount of motion of an imaging element 104, with a predetermined threshold value. Thereby, the control unit 106 determines whether or not the second image can be acquired (step S604). The processing of step S604 is similar to the processing of step S304 shown in FIG. 13.

In step S604, when the amount of motion is greater than the threshold value, the control unit 106 determines that the second image cannot be acquired. In this case, the processing of step S602 is executed. In step S604, when the amount of motion is less than the threshold value, the control unit 106 determines that the second image can be acquired. In this case, the second image is acquired (step S605). The processing of step S605 is similar to the processing of step S108 shown in FIG. 3.

After step S605, the measurement processing unit 111 executes a measurement process on the basis of the first image and the second image and outputs a measurement result to the control unit 106 (step S606). In step S606, the measurement processing unit 111 measures at least one of a subject shape and a subject distance. In step S606, the measurement processing unit 111 detects an amount of parallax between the first image and the second image during the measurement process.

After step S606, the validity determination unit 113 reads a table from a frame memory 107. The validity determination unit 113 obtains an allowable threshold value corresponding to the amount of parallax detected in step S606 from the table. The validity determination unit 113 executes a validity determination. That is, the validity determination unit 113 determines the validity of the measurement result by comparing the amount of motion detected in step S603 with the allowable threshold value (step S607). In the determination of step S607, a table similar to the table shown in FIG. 16 is used.

In step S607, when the amount of motion is greater than the allowable threshold value, the validity determination unit 113 determines that the measurement result is not valid. In this case, the processing of step S601 is executed. In step S607, when the amount of motion is less than the allowable threshold value, the validity determination unit 113 determines that the measurement result is valid. In this case, the measurement is completed.

The threshold value used for the determination of step S604 may be a threshold value according to a subject distance. For example, when the processing of step S604 is initially executed, a predetermined initial value is used as the threshold value. In the subsequent processing of step S604, a threshold value according to the subject distance measured in step S606 is used. The processing of step S604 is not necessary.

As in the third embodiment, the measurement device 12 of the fourth embodiment can secure a desired measurement accuracy and increase a frequency of execution of measurement. Also, because a processing system for detecting the amount of parallax does not need to be independent from the measurement processing unit 111, the processing system can be simplified as in the third embodiment.

Modified Example of Fourth Embodiment

In the modified example of the fourth embodiment, a frame memory 107 does not need to store a table in which amounts of parallax and allowable threshold values are associated. A validity determination unit 113 calculates an allowable threshold value corresponding to an amount of parallax detected by a measurement processing unit 111 on the basis of an amount of errors in a result of a measurement process. The amount of errors of the result of the measurement process is predetermined for each amount of parallax.

An allowable error rate ErrorRate(Z) of a subject distance for each amount of parallax d is predetermined as a specification, i.e., the allowable error rate ErrorRate(Z) is set to a constant. In step S607 shown in FIG. 19, the validity determination unit 113 calculates an allowable threshold value of an amount of parallax change $\Delta d$ for each amount of parallax d detected in step S606 by Equation (9). The validity determination unit 113 determines the validity of the measurement result by comparing the amount of motion detected in step S603 with the calculated allowable threshold value.

As described above, the validity determination unit 113 calculates an allowable threshold value corresponding to the amount of parallax every time the validity of the measurement result is determined. Thus, the frame memory 107 does not need to store a table in which amounts of parallax and allowable thresholds value are associated.

(Additional Statement)

According to one aspect of the present invention, a measurement device includes an imaging unit, a motion detection unit, a measurement processing unit, and a validity determination unit. The imaging unit captures a first subject image via a first objective optical system at a first imaging timing. The imaging unit captures a second subject image via a second objective optical system at a second imaging timing different from the first imaging timing. The imaging unit generates a first image based on the first subject image. The imaging unit generates a second image based on the second subject image. The second objective optical system is arranged to have parallax with respect to the first objective optical system. The motion detection unit detects an amount of motion of the imaging unit. The measurement processing unit executes a measurement process on the basis of the first image and the second image and detects an amount of parallax between the first image and the second image in the measurement process. The validity determination unit determines validity of a result of the measurement process by comparing the amount of motion with an allowable threshold value according to the amount of parallax.

According to one aspect of the present invention, a method for operating a measurement device includes a first imaging step, a second imaging step, a subject distance detection step, a motion detection step, a measurement availability determination step, and a measurement processing step. The measurement device has an imaging unit. In the first imaging step, the imaging unit captures a first subject image via a first objective optical system at a first imaging timing and generates a first image based on the first subject image. In the second imaging step, the imaging unit captures a second subject image via a second objective optical system at a second imaging timing different from the first imaging timing and generates a second image based on the second subject image. The second objective optical system is arranged to have parallax with respect to the first objective optical system. In the subject distance detection step, a subject distance is detected. In the motion detection step, an amount of motion of the imaging unit is detected. In the measurement availability determination step, it is determined whether or not measurement is executable by comparing the amount of motion with an allowable threshold value according to the subject distance. In the measurement processing step, a measurement process is executed on the basis of the first image and the second image when it is determined that the measurement is executable in the measurement availability determination step.

According to one aspect of the present invention, a method for operating a measurement device includes a first imaging step, a second imaging step, a parallax detection step, a motion detection step, a measurement availability determination step, and a measurement processing step. The measurement device has an imaging unit. In the first imaging step, the imaging unit captures a first subject image via a first objective optical system at a first imaging timing and generates a first image based on the first subject image. In the second imaging step, the imaging unit captures a second subject image via a second objective optical system at a second imaging timing different from the first imaging timing and generates a second image based on the second subject image. The second objective optical system is arranged to have parallax with respect to the first objective optical system. In the parallax detection step, an amount of parallax between the first image and the second image is detected. In the motion detection step, an amount of motion of the imaging unit is detected. In the measurement availability determination step, it is determined whether or not measurement is executable by comparing the amount of motion with an allowable threshold value according to the amount of parallax. In the measurement processing step, a measurement process is executed on the basis of the first image and the second image when it is determined that the measurement is executable in the measurement availability determination step.

According to one aspect of the present invention, a method for operating a measurement device includes a first imaging step, a second imaging step, a motion detection step, a measurement processing step, and a validity determination step. The measurement device has an imaging unit. In the first imaging step, the imaging unit captures a first subject image via a first objective optical system at a first imaging timing and generates a first image based on the first subject image. In the second imaging step, the imaging unit captures a second subject image via a second objective optical system at a second imaging timing different from the first imaging timing and generates a second image based on the second subject image. The second objective optical system is arranged to have parallax with respect to the first objective optical system. In the motion detection step, an amount of motion of the imaging unit is detected. In the measurement processing step, a measurement process is executed on the basis of the first image and the second image and detecting a subject distance in the measurement process. In the validity determination step, validity of a result of the measurement process is determined by comparing the amount of motion with an allowable threshold value according to the subject distance.

According to one aspect of the present invention, a method for operating a measurement device includes a first imaging step, a second imaging step, a motion detection step, a measurement processing step, and a validity determination step. The measurement device has an imaging unit. In the first imaging step, the imaging unit captures a first subject image via a first objective optical system at a first imaging timing and generates a first image based on the first subject image. In the second imaging step, the imaging unit captures a second subject image via a second objective optical system at a second imaging timing different from the first imaging timing and generates a second image based on the second subject image. The second objective optical system is arranged to have parallax with respect to the first objective optical system. In the motion detection step, an amount of motion of the imaging unit is detected. In the measurement processing step, a measurement process is executed on the basis of the first image and the second image and an amount of parallax between the first image and the second image is detected in the measurement process. In the validity determination step, validity of a result of the measurement process is determined by comparing the amount of motion with an allowable threshold value according to the amount of parallax.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A measurement device, comprising:
   an image sensor configured to capture a first subject image via a first objective optical system at a first imaging timing, capture a second subject image via a second objective optical system at a second imaging timing different from the first imaging timing, generate a first image based on the first subject image, and generate a second image based on the second subject image, the second objective optical system being arranged to have parallax with respect to the first objective optical system;
   a motion sensor configured to detect an amount of motion of the image sensor;
   a processor configured to:
      detect a subject distance between the image sensor and the subject;
      determine whether or not measurement is executable by comparing the amount of motion with an allowable threshold value according to the subject distance; and
      execute a measurement process on the basis of the first image and the second image in response to a determination that the measurement is executable.

2. The measurement device according to claim 1, wherein the processor is configured to detect the subject distance by at least one of stereo measurement using the first image and the second image and laser length measurement.

3. The measurement device according to claim 1, wherein the motion sensor detects the amount of motion by detecting an amount of displacement between a plurality of the first images.

4. The measurement device according to claim 1, wherein the motion sensor is at least one of an acceleration sensor and a gyro sensor.

5. The measurement device according to claim 1, further comprising:
   a memory configured to store a table in which the subject distance and the allowable threshold value are associated,
   wherein the processor is configured to acquire the allowable threshold value corresponding to the subject distance from the table.

6. The measurement device according to claim 1, wherein the processor is configured to calculate the allowable threshold value corresponding to the subject distance on the basis of an amount of errors in a result of the measurement process, the amount of errors being predetermined for each subject distance.

7. The measurement device according to claim 1, wherein a first allowable threshold value as the allowable threshold value corresponding to a first subject distance is greater than a second allowable threshold value as the allowable threshold value corresponding to a second subject distance greater than the first subject distance.

8. A measurement device, comprising:
an image sensor configured to capture a first subject image via a first objective optical system at a first imaging timing, capture a second subject image via a second objective optical system at a second imaging timing different from the first imaging timing, generate a first image based on the first subject image, and generate a second image based on the second subject image, the second objective optical system being arranged to have parallax with respect to the first objective optical system;
a motion sensor configured to detect an amount of motion of the image sensor;
a processor configured to:
detect an amount of parallax between the first image and the second image;
determine whether or not measurement is executable by comparing the amount of motion with an allowable threshold value according to the amount of parallax; and
execute a measurement process on the basis of the first image and the second image in response to a determination that the measurement is executable.

9. The measurement device according to claim 8, further comprising:
a memory configured to store a table in which the amount of parallax and the allowable threshold value are associated,
wherein the processor is configured to acquire the allowable threshold value corresponding to the amount of parallax detected by the parallax detection unit from the table.

10. The measurement device according to claim 8, wherein the processor is configured to calculate the allowable threshold value corresponding to the amount of parallax on the basis of an amount of errors in a result of the measurement process, the amount of errors being predetermined for each amount of parallax.

11. The measurement device according to claim 8, wherein a first allowable threshold value as the allowable threshold value corresponding to a first amount of parallax is greater than a second allowable threshold value as the allowable threshold value corresponding to a second amount of parallax less than the first amount of parallax.

12. A measurement device, comprising:
an image sensor configured to capture a first subject image via a first objective optical system at a first imaging timing, capture a second subject image via a second objective optical system at a second imaging timing different from the first imaging timing, generate a first image based on the first subject image, and generate a second image based on the second subject image, the second objective optical system being arranged to have parallax with respect to the first objective optical system;
a motion sensor configured to detect an amount of motion of the image sensor;
a processor configured to:
execute a measurement process on the basis of the first image and the second image and detect a subject distance between the image sensor and the subject in the measurement process; and
determine validity of a result of the measurement process by comparing the amount of motion with an allowable threshold value according to the subject distance.

* * * * *